(12) United States Patent
Bose et al.

(10) Patent No.: US 10,456,103 B2
(45) Date of Patent: Oct. 29, 2019

(54) UNIFIED TRAJECTORY GENERATION PROCESS AND SYSTEM

(71) Applicant: SHANGHAI UNITED IMAGING HEALTHCARE CO., LTD., Shanghai (CN)

(72) Inventors: Supratik Bose, Concord, CA (US); Johannes Stahl, Concord, CA (US); Jonathan Maltz, Concord, CA (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 622 days.

(21) Appl. No.: 15/182,080

(22) Filed: Jun. 14, 2016

(65) Prior Publication Data
US 2017/0354393 A1    Dec. 14, 2017

(51) Int. Cl.
*A61B 6/00* (2006.01)
*A61N 5/10* (2006.01)

(52) U.S. Cl.
CPC ............ *A61B 6/547* (2013.01); *A61N 5/1036* (2013.01); *A61N 5/1047* (2013.01); *A61N 2005/1074* (2013.01)

(58) Field of Classification Search
None
See application file for complete search history.

(56) References Cited

U.S. PATENT DOCUMENTS

| | | | |
|---|---|---|---|
| 5,179,514 | A | 1/1993 | Rastegar et al. |
| 6,216,058 | B1 | 4/2001 | Hosek et al. |
| 7,130,716 | B2 | 10/2006 | Rogers et al. |
| 8,027,431 | B2 | 9/2011 | Stahl et al. |
| 8,290,611 | B2 | 10/2012 | Sladek et al. |

(Continued)

FOREIGN PATENT DOCUMENTS

CN    1953782 A    4/2007

OTHER PUBLICATIONS

The extended European search report in European Application No. 17178521.5 dated Oct. 13, 2017, 9 pages.

(Continued)

*Primary Examiner* — Hoon K Song
(74) *Attorney, Agent, or Firm* — Metis IP LLC

(57) ABSTRACT

A system, medium, and method including obtaining a plurality of positions for multiple components defined by a plan; obtaining a set of constraints that express limitations for the multiple components at the plurality of positions, the constraints being applicable to a plan where the multiple components synchronously change their positions with time to traverse a prescribed sequence of the plurality of positions, at least one of the multiple components being further constrained to change its position over time by staying within a predefined tolerance to a predefined smooth function of position over time between different positions; determining a trajectory of position and a minimum duration in which the multiple components completely synchronously traverse the prescribed sequence of positions while satisfying the constraints for the multiple components; and generating a record of the determined trajectory of position and the minimum duration for the plurality of components.

35 Claims, 7 Drawing Sheets

(56) References Cited

U.S. PATENT DOCUMENTS

| | | | |
|---|---|---|---|
| 8,295,435 B2* | 10/2012 | Wang | A61N 5/10 378/65 |
| 2008/0123813 A1 | 5/2008 | Maurer et al. | |
| 2008/0226030 A1 | 9/2008 | Otto | |
| 2009/0225942 A1 | 9/2009 | Shepard et al. | |
| 2010/0046706 A1 | 2/2010 | Moreau | |
| 2010/0322381 A1 | 12/2010 | Stahl et al. | |
| 2011/0186755 A1 | 8/2011 | Otto | |
| 2013/0216026 A1 | 8/2013 | Nord et al. | |
| 2013/0324784 A1* | 12/2013 | Fredriksson | A61N 5/1031 600/1 |

OTHER PUBLICATIONS

Otto K., Volumetric modulated arc therapy: IMRT in a single gantry arc, Medical Physics, 35(1): 310-317, 2008.

Kjaer-Kristoffersen F et al., RapidArc volumetric modulated therapy planning for prostate cancer patients, Acta Oncologica, 48: 227-232, 2009.

Bedford J L., Treatment planning for volumetric modulated arc therapy, Medical Physics, 36(11): 5128-5138, 2009.

Bill J Salter et al., Rotational IMRT delivery using a digital linear accelerator in very high dose rate burst mode delivery, Medical Physics, 56: 1931-1946, 2011.

D. Rangaraj et al., Fundamental properties of the delivery of volumetric modulated arc therapy (VMAT) to static patient anatomy, Medical Physics, 37(8): 4057-4067, 2010.

Chun-Shin Lin et al., Formulation and Optimization of Cubic Polynomial Joint Trajectories for Industrial Robots, IEEE Transactions on Automatic Control, 28(12): 1066-1074, 1983.

Chi-Hsu Wang et al., Constrained minimum-time path planning for robot manipulators via virtual knots of the cubic B-spline functions, IEEE Transactions on Automatic Control, 35(5): 573-577, 1990.

Kruger CJC, Constrained cubic spline interpolation, Chemical Engineering Applications, 2003.

Iravani P. et al., Variable-velocity exponential input shaping for position controlled robotic systems, Proceedings of the ASME 2010 Dynamic Systems and Control Conference, 2010.

Rymansaib, Z. et al., Exponential Trajectory Generation for Point to Point Motions, IEEE/ASME International Conference on Advanced Intelligent Mechatronics (AIM), 2013.

Wijesooriya K. et al., Determination of maximum leaf velocity and acceleration of a dynamic multileaf collimator: Implications for 4D radiotherapy, Medical Physics, 32(4): 932-941, 2005.

Song Y. et al., Dosimetric effects of gantry angular acceleration and deceleration in volumetric modulated radiation therapy, International Federation for Medical and Biological Engineering (IFMBE) Proceedings, 25: 1046-1050, 2009.

Amendola B. E. et al., Volumetric-modulated arc therapy with RapidArc : An evaluation of treatment delivery efciency, Reports of practical oncology and radiotherapy, 18:383-386, 2013.

Calippe Serge, RapidArc workshop Session 1(a), RapidArc workshop, Jan. 27-28, 2012.

Konar T. S. et al., Integration of $e^{\wedge}(x^{\wedge}n)$ and $e^{\wedge}((-x)^{\wedge}n)$ in forms of series, their applications in the eld of di erential equation; introducing generalized form of Skewness and Kurtosis; extension of starling's approximation, Eprint arXiv:0803.2736, 2008.

\* cited by examiner

500

```
┌─────────────────────────────────────────────┐
│ OBTAIN A PLURALITY OF ONE-DIMENSIONAL       │
│ POSITIONS DEFINED BY A RADIOTHERAPY         │
│ TREATMENT PLAN                              │
│                                         505 │
└─────────────────────────────────────────────┘
                      │
                      ▼
┌─────────────────────────────────────────────┐
│ OBTAIN A SET OF POSITION RELATED CONSTRAINTS│
│ FOR A PLURALITY OF MECHANICAL AND RADIATION │
│ PRODUCING COMPONENTS OF A RADIATION         │
│ TREATMENT DELIVERY SYSTEM FOR DELIVERING A  │
│ RADIOTHERAPY TREATMENT PLAN BY SYNCHRONOUS  │
│ MOTION OF THE PLURALITY OF MECHANICAL AND   │
│ RADIATION PRODUCING COMPONENTS TRAVERSING   │
│ A PRESCRIBED SEQUENCE OF THE PLURALITY      │
│ OF POSITIONS IN A PREDETERMINED TIME    510 │
└─────────────────────────────────────────────┘
                      │
                      ▼
┌─────────────────────────────────────────────┐
│ DETERMINE A TRAJECTORY AND A MINIMUM        │
│ DURATION FOR THE RADIATION TREATMENT        │
│ DELIVERY SYSTEM TO TRAVERSE THE PRESCRIBED  │
│ SEQUENCE OF THE PLURALITY OF POSITIONS AND  │
│ DELIVER THE RADIOTHERAPY TREATMENT PLAN     │
│ WHILE ADHERING TO THE CONSTRAINTS AND BEING │
│ WITHIN A PREDETERMINED TOLERANCE LIMIT OF   │
│ A LINEAR TRAJECTORY ALONG THE PRESCRIBED    │
│ SEQUENCE OF THE PLURALITY OF POSITIONS      │
│                                         515 │
└─────────────────────────────────────────────┘
                      │
                      ▼
┌─────────────────────────────────────────────┐
│ CONTROL THE PLURALITY OF MECHANICAL AND     │
│ RADIATION PRODUCING COMPONENTS OF THE       │
│ RADIATION TREATMENT DELIVERY SYSTEM TO      │
│ EXECUTE THE DETERMINED TRAJECTORY WITHIN    │
│ THE DETERMINED MINIMUM DURATION             │
│                                         520 │
└─────────────────────────────────────────────┘
```

FIG. 5

UNIFIED TRAJECTORY GENERATION PROCESS AND SYSTEM

BACKGROUND

Field

The embodiments described below generally relate to controlling a radiation therapy delivery system. More specifically, some embodiments relate to generating a unified trajectory for a radiation therapy delivery system and controlling the system in accordance therewith.

Description

Contemporary radiotherapy treatment planning systems may provide specialized versions of step-and-shoot intensity modulated radiotherapy (IMRT) and arc based IMRT. Some notable examples are Varian's RapidArc (Varian Medical Systems, Palo Alto, Calif., USA), Elekta's VMAT (Elekta Ltd, Crawley, UK), and Siemens' Modulated Arc (mARC) (Siemens AG Healthcare, Erlangen, Germany). In some aspects, during the treatment planning process parameters such as gantry speed, leaf speed, dose rate, and the limits on the bounds of such quantities are considered. The treatment plans are then passed to a linac (i.e., a linear accelerator of the radiation treatment delivery system) controller as a collection of discrete control points. Each of the control points describes the simultaneous position of each mechanical component of the linac, as well as the cumulative delivered dose of radiation up to that instant.

When the radiation treatment delivery system is in an intermediate state between control points, it is implicitly assumed that the components of the delivery system move with a constant velocity that results in a linear trajectory of movement between the control points. As used herein, a linear trajectory implies a one dimensional or angular position trajectory that is linear over time. It is not a straightforward process to determine the delivery parameters, as a function of time, that would ensure that the implicit piecewise linear trajectory of the radiation delivery system components in between the control points is faithfully executed, while not prohibitively prolonging the delivery process. This may be due, at least in part, because an ideal piecewise linear trajectory between successive "segments" will require infinite acceleration at the control point. Otherwise, one can use a very small acceleration to achieve a low constant velocity that will ensure linearity but at the cost of increasing delivery time.

Additionally, this is not a trivial concern since, for example, specification of a linear trajectory between two points for one component may result in longer delivery times for the system as a whole.

Conventionally, the delivery parameters may be decided locally for individual segments, as opposed to optimum delivery parameters considering the whole trajectory. For example, for a particular type of treatment the controller may attempt to deliver the treatment of each segment (or partial arc) with a constant dose rate and constant gantry speed. The linked delivery parameters (e.g., cumulative output monitor units (MU), radiation output rate and the gantry speed, etc.) of each segment are pre-computed using, for example, the following heuristics of:

1. If the MU value is large, then the controller tries to deliver the treatment plan using the maximum dose rate while varying gantry speed.

2. When a smaller number of MUs are to be delivered, the controller tries to use the maximum gantry speed while varying the dose rate.

3. For intermediate MU ranges, the controller varies both the dose rate and the gantry speed. In all cases, the chosen gantry speed and the dose rate are chosen in such a way that the resultant duration is sufficient for the multileaf collimator (MLC) or other beam-shaping device(s) to change their shape to accommodate all segments.

In one previous attempt to obtain the optimum delivery parameters that might result in a minimum beam-on time by establishing their interrelationships and solving an optimization problem, neither the acceleration and the jerk capability of the system nor the constraints on the different components are explicitly treated or modeled by the delivery system vendors. As a result, the smoothness of the treatment delivery cannot be guaranteed. Instead, the gantry position, the leaf positions, and the cumulative dose output by the system are monitored periodically (e.g., every 50 ms in Varian's RapidArc) and online adjustments are made in order to try to stay close to the piecewise linear trajectory of the treatment plan.

In much of the previous work regarding the trajectory of robotic manipulators, splines and variants thereof are used as trajectory models. While spline and spline-like functions might succeed at maintaining via-point accuracy and providing smooth trajectories, these functions tend to ripple (oscillate) and depart significantly from a linear trajectory. In some regards, a constrained cubic spline method has been developed that attempts to tackle an overshoot problem. However, constrained splines result in discontinuous acceleration(s) at via points. Additionally, attempts to realize such non-physical trajectories may lead to excessive mechanical wear and excitation of higher system modes that lead to further inaccuracies.

A trapezoidal velocity model has been widely used in industry for standard position control of some mechanical components. However, such a model requires discontinuous acceleration and infinite jerk to realize trajectories. In some instances, instead of a spline based model for position or a trapezoidal velocity model, an exponential velocity model (EVM) has been used to obtain a trajectory for a single component that passes through multiple via points, while maintaining velocity, acceleration, and jerk constraints. The EVM has some advantage over the trapezoidal velocity model owing to the continuous nature of its velocity, acceleration and jerk profiles. Also, unlike commonly employed 3rd-order spline based position models, it exhibits less over- and undershoot, and realizes a continuous jerk profile. However, some disadvantages of the EVM include, for example, the computed trajectories are unnecessarily slow since maximum acceleration and jerk are not maintained for as long as possible, and the position trajectories cannot be expressed in an analytical closed form. An infinite series expression is, however, available for the position trajectory. In some aspects, time-optimal velocity profiles are constructed for each "segment" and the velocity profiles are then modified so that the final velocity of a segment blends into the initial velocity of the next segment. However, no attempt is made to optimize the total time or to keep the position trajectory within tolerance of a predefined specification thereof.

Improved control of a radiation treatment delivery system to provide an optimal delivery duration and close observance to the linear trajectory of a treatment plane is desired, with all of the constraints of position for the radiation treatment delivery system being considered and satisfied.

The above arguments apply also to diagnostic imaging systems. In such systems, one or more sources of ionizing and non-ionizing radiation may be required to move synchronously with one or more imaging detectors, and also the patient support (couch, table, platform or seat). Usually, the synchrony must also include the delivered imaging radiation rate and amount. The teachings contained herein apply equally to such systems. In general, references to the linear accelerator, the radiation source, apply also to radioisotope sources, diagnostic imaging x-ray tube sources, sources of ultrasound, and electromagnetic fields such as those used in magnetic resonance imaging.

SUMMARY

In order to address the foregoing, some embodiments provide a system, medium, and method including obtaining a set of position related constraints for a plurality of mechanical and radiation producing components of a radiation treatment delivery system, the constraints applicable to the radiation treatment delivery system delivering the radiotherapy treatment plan by synchronous motion of the plurality of mechanical and radiation producing components traversing a prescribed sequence of the plurality of positions in a predetermined time; determining a trajectory and a minimum duration for the radiation treatment delivery system to traverse the prescribed sequence of the plurality of positions and deliver the radiotherapy treatment plan while adhering to the constraints and being within a predetermined tolerance limit of a linear trajectory along the prescribed sequence of the plurality of positions; and controlling the plurality of mechanical and radiation producing components of the radiation treatment delivery system to execute the determined trajectory within the determined minimum duration, as indicated in the record.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein:

FIG. 5 is an illustrative depiction of some aspects of a step-and-shoot treatment plan, in accordance with some embodiments

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
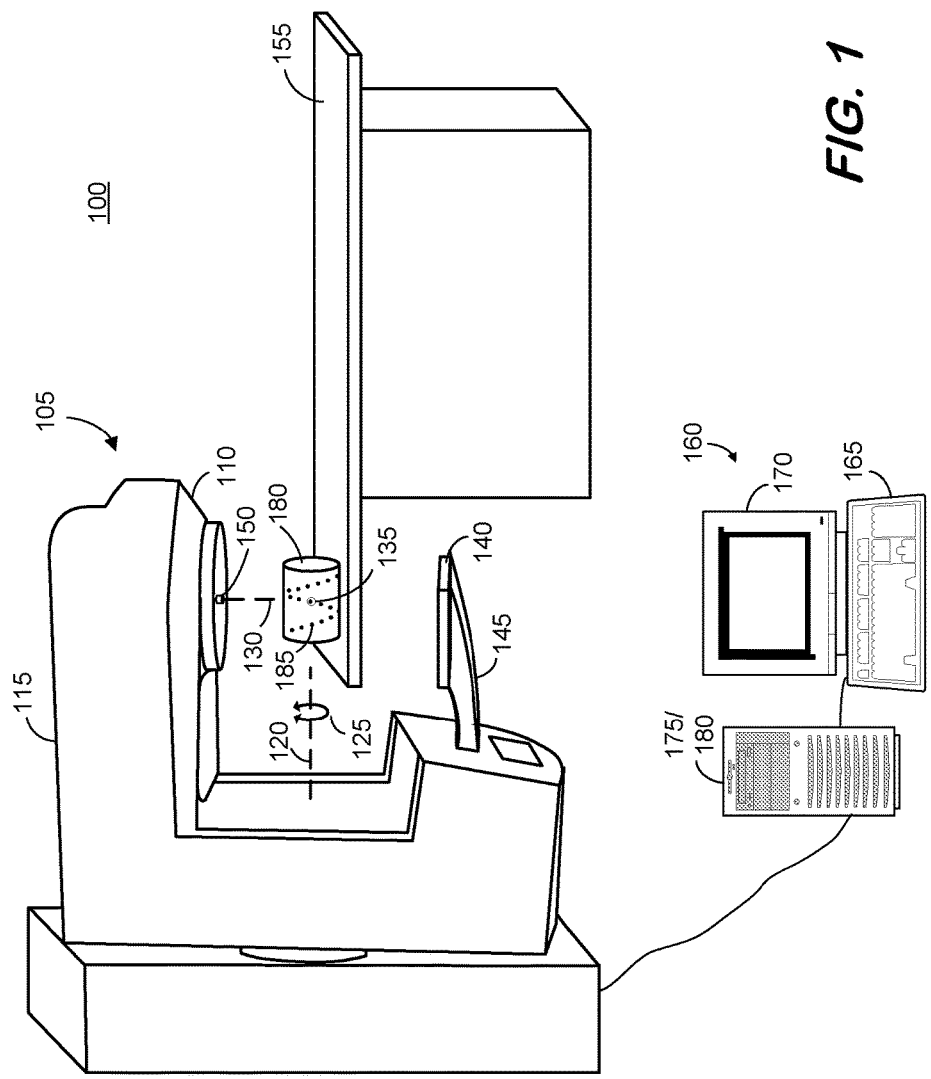
FIG. 1 is a perspective view of a radiation treatment room, compatible with some embodiments.

FIG. 1 illustrates radiotherapy treatment room 100 that may provide a context for some aspects, contexts, use-cases or platforms of the present disclosure, according to some embodiments. Radiotherapy treatment room 100 includes linear accelerator (linac) 105, table 155 and operator console 160. The various components of radiotherapy treatment room 100 may be used to deliver a beam of radiation to a target volume such as phantom 180. The target volume may comprise a patient positioned to receive the beam according to a radiation treatment plan. The elements of treatment room 100 may be employed in other applications according to some embodiments.

Linac 105 generates and emits a radiation beam (e.g., an x-ray beam) from treatment head 110. More particularly, the radiation originates at radiation source 150. The radiation beam may comprise electron, photon or any other type of radiation. According to some embodiments, the beam exhibits energies in the megavoltage range (i.e. >1 MeV) and may therefore be referred to as megavoltage beam.

Treatment head 110 is coupled to a projection of gantry 115. Gantry 115 is controllable to be rotatable around gantry axis 120. As indicated by arrow 125, gantry 115 may rotate clockwise or counter-clockwise according to some embodiments. Rotation of gantry 115 serves to rotate treatment head 110 around axis 120.

During radiation emissions (e.g., treatment, calibration, and other procedures) treatment head 110 emits a divergent beam of megavoltage x-rays along beam axis 130. The beam is emitted towards isocenter 135 of linac 105. Isocenter 135 may be located at the intersection of beam axis 130 and gantry axis 120. Due to divergence of the beam and the shaping of the beam by beam-shaping devices in treatment head 110, the beam may deliver radiation to a volume of phantom 180 rather than only through isocenter 135.

Table 155 may support a patient during radiation treatment and support phantom 180 during aspects discussed herein. Table 155 may be adjustable to assist in positioning phantom 180 or a particular target volume of a patient at isocenter 135. Table 155 may also be used to support devices used for such positioning, for calibration and/or for verification.

Imaging device 140 may comprise any system to acquire an image based on received radiation. Imaging device 140 may be attached to gantry 115 in any manner, including an extendible and retractable housing 118. Rotation of gantry 115 may cause treatment head 110 and imaging device 140 to rotate around isocenter 135 such that isocenter 135 remains located between treatment head 110 and imaging device 140 throughout stationary and rotational movements of gantry 115.

Imaging device 140 may acquire projection images before, during and/or after radiation treatment. In some embodiments, imaging device 140 may include an analog or a digital radiation detector. Imaging device 140 may be used to acquire images based on radiation emitted from treatment head 110. These images may reflect the attenuative properties of objects located between treatment head 110 and imaging device 140.

Radiation source 150 may include any sources to emit kilovoltage radiation or other imaging radiation that are or become known. In some embodiments, radiation source 150 may employ a cathode based on carbon nanotube or thermionic emission technology. In some embodiments, each radiation source 150 may be disposed in a fixed relationship with respect to treatment head 110.

It is noted that the source-detector trajectory of the radiotherapy system including the imaging system may be controlled, in some embodiments, to move in a circular or non-circular trajectory and/or have a fixed or variable radiation source detector distance.

Operator console 160 includes input device 165 for receiving instructions from an operator such as an instruction to calibrate linear accelerator 105 and an instruction to move radiation source 150 in a particular trajectory and to deliver radiation from a number of discrete positions or locations along the trajectory path, according to a trajectory path of a radiotherapy treatment plan and a velocity model. Console 160 also includes output device 170 that may include a monitor for presenting calculated projection images, acquired projection images, three-dimensional images, operational parameters of linear accelerator 105 and/or interfaces for controlling elements thereof. Input device 165 and output device 170 are coupled to processor 175 and storage 180.

Processor 175 executes program instructions or code according to some embodiments. The program instructions may be executable to control linear accelerator 105 to operate as described herein. The program instructions may be stored in storage 180, which may comprise one or more tangible storage media of identical or different types, including but not limited to a fixed disk, a floppy disk, a CD-ROM, a DVD-ROM, an optical disk or storage device, a magnetic tape, a solid state storage device, a flash drive, and a other devices and systems. Storage 180 may store, for example, virtual models of phantoms, initial imaging geometry parameters, radiation treatment plans, set(s) of position related constraints for the plurality of mechanical and radiation producing components of the radiation treatment system 105, software applications to control (e.g., calibrate, etc.) linear accelerator 105 and/or to provide radiation treatment, and other data used to perform radiation treatment.

Operator console 160 may be located apart from linear accelerator 105, such as in a different room, in order to protect its operator or other entity from radiation. For example, linear accelerator 105 may be located in a heavily shielded room, such as a concrete vault, which shields the operator from radiation generated by accelerator 105.

Each of the devices shown in FIG. 1 may include fewer, more, or different elements than those shown and are not limited to the devices shown in FIG. 1.

In external beam radiotherapy, treatment delivery is modeled as the synchronous actuation of multiple mechanical and radiation producing components through a prescribed sequence of discrete states, also known as "control points". In-between the control points, the motion is constrained but unspecified and depends upon the implementation of specific delivery modes (e.g., step-and-shoot, modulated arc, etc.). The present disclosure includes processes to generate a continuous position versus time trajectory that enables direct control of the trade-off between delivery accuracy and delivery time.

The present disclosure introduces a number of innovations to achieve such an optimized trajectory. In some aspects, the processes herein include, for any component that follows a general class of one dimensional (1-D) velocity models containing three phases (monotonic increase (or decrease), constant velocity, and monotonic decrease (or increase)) of velocity, a process to determine the minimum duration, as well as the feasibility of a given duration for a position trajectory of satisfying three sets of constraints for the mechanical and radiation producing components of the radiation treatment system is presented herein.

A first set of constraints, Set I, includes boundary conditions, as well as constraints on total execution time and distance, including an entry velocity, an entry acceleration (zero), an exit velocity, an exit acceleration (zero), a time taken to execute the trajectory, and a distance between entry and exit positions.

A second set of constraints, Set II, may include derivatives of the position of the mechanical and radiation producing components of the radiation treatment system during the trajectory. Set II can include the constraints of a jerk parameter, an acceleration parameter, and a velocity.

A third set of constraints, Set III, can include and consider trajectory tolerance(s) that constrain a generated position trajectory to stay within a pre-defined tolerance limit of the linear position trajectory of the radiation treatment plan over time between two positions (i.e., control points). If such a trajectory is feasible, then a process herein may be used to determine a cruise velocity and the durations for the acceleration, cruise, and deceleration intervals of the trajectory between the two positions.

In some aspects herein, in response to a need to enforce the constraint conditions of Sets I-III, an optimization process is disclosed to determine the position trajectories of, for example, linear accelerator (linac) components (including machine radiation output rate and its derivatives) with a goal to minimize a total duration of delivery while satisfying all of the constraints.

In some embodiments, in the instance of an interruption of a treatment delivery, a process for the fast computation of a resumption trajectory that catches up with the calculated/determined optimized trajectory within few control points is disclosed herein. Accordingly, the interrupted calculated/determined optimized trajectory may be resumed within traversing a few control points.

In some aspects herein, the present disclosure demonstrates a possible trade-off between delivery accuracy and delivery time that may be used to speed-up delivery of conventional step-and-shoot treatments by allowing some mechanical components to move during short intervals within a prescribed tolerance (as opposed to being static as is the case in conventional step-and-shoot contexts).

Accordingly, optimized trajectories have been realized by using the processes disclosed herein, with the results being confirmed by comparison to, for example, the average delivery times reported by the radiation treatment delivery system's manufacturer. In some instances, a resumption trajectory was computed from the point of interruption that enabled a resumption of the original trajectory (i.e., catch-up) within, for example, 4 control points. In other aspects, Applicant has realized in the context of a step-and-shoot treatment plan with, for example, 71 segments, how one can generate a trajectory that reduces a planned delivery time by about 15% by allowing the gantry to move within some tolerance during the shoot segments.

In some aspects, the present disclosure presents a framework and processes to achieve fast synchronized movement of multiple mechanical components via predefined positions (i.e., control points) while satisfying all mechanical constraints and without significant reduction in positional accuracy. The presented framework, when applied in radiotherapy treatment delivery, also allows the designers and other entities to implement original and hybrid therapy modes without the need to develop specific automation strategies.

In some aspects, the problem of determining the delivery parameters may be approached from the perspective of trajectory generation for robotic manipulators. In robotics, the generation of the time-optimum simultaneous trajectory of multiple manipulators between "via points", while respecting velocity, acceleration, and jerk constraints, is well studied for certain specific models of position and velocity. In the problem formulation herein, we identify a via point of a robotic manipulator end-point trajectory with a control point of a radiotherapy delivery. Some of the methods presented herein obtain the trajectory of delivery system components by formulating a trade-off between the overall delivery time and the degree to which the generated trajectory conforms to a model piecewise linear trajectory. Presented hereinbelow is a brief review of some aspects of trajectory generation for robotic manipulators and a discussion of its limitations to the problem of trajectory generation of radiation therapy delivery system (RTDS) components during treatment delivery that are more broadly addressed herein.

Figure 2:
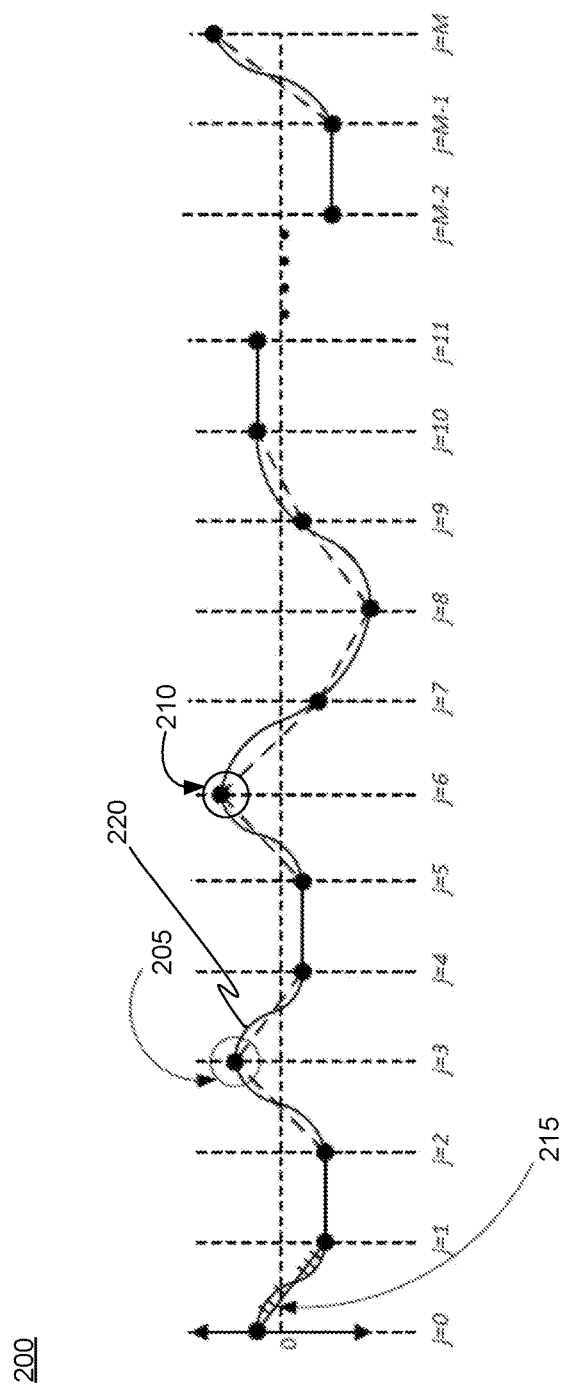
FIG. 2 is a depiction of a trajectory, illustrating some aspects of a radiotherapy treatment plan.

Some of the shortcomings of some other approaches regarding trajectory generation for a RTDS (radiation therapy delivery system) may include emphasizing generating time-optimal trajectories and via-point accuracy without constraining trajectories to remain within a tolerance of some predefined (e.g., linear) trajectory in between via points. FIG. 2 is an illustrative depiction of a trajectory 200 including a plurality of via points such as, for example, points 205 and 210. The trajectory model is shown as comprising a piece-wise linear trajectory at 215. The actual trajectory is shown at 220. Seen in FIG. 2 is the deviation or difference between the piecewise linear trajectory model's profile between the via points and the actual robotic motion shown at 220.

In some aspects, each of the spline, trapezoidal, and EVM approaches are tied to some specific position or velocity model. As such, these and other approaches do not provide a generic framework that is applicable to a large class of velocity (and acceleration and jerk) models for moving linked components that obtains a simultaneous time-optimal trajectory for the components, while remaining within a certain tolerance of some specified trajectory.

In some embodiments, the present disclosure addresses some of the inadequacies of other approaches and provides a trajectory generation framework involving a number of unique features. These features include, for motion between two 1-D positions involving a generic class of velocity model that contains an interval of monotonic increase (or decrease), a constant velocity interval, and an interval of monotonic decrease (or increase, respectively). A process is disclosed that can determine both a minimum duration, as well as the feasibility of a given duration for a position trajectory satisfying a plurality (i.e., set) of constraints. In some embodiments, the set of constraints include an entry and exit velocity; the predefined duration and distance between the two points; an entry and exit acceleration that are both set to zero; and jerk, acceleration, and velocity parameters that are constrained (i.e., bound). Furthermore, the generated position trajectory stays within a predefined tolerance limit of the linear trajectory over time. If such a trajectory is feasible, then a process herein provides a mechanism to determine a cruise velocity and durations for the acceleration, cruise and deceleration intervals.

Regarding the generic class of velocity model, a number of different velocity models, including but not limited to, a trapezoidal velocity model, a linear position trajectory with polynomial blend, a double-S velocity model, and a 15-segment trajectory or EVM are within this category.

The present disclosure also relates to and presents, using the process(es) introduced above as a basis, a process to determine 1-D position trajectories of the mechanical components and the dose of any generic radiotherapy treatment plan such that the components move synchronously between consecutive control points while respecting all constraints on position, velocity, acceleration and jerk while minimizing the total duration of delivery.

Some aspects herein relate to a scenario wherein the delivery of a trajectory optimized as disclosed herein is interrupted. In such cases, the present disclosure provides a process for a fast computation of a resumption trajectory that returns or catches up with the pre-computed optimized trajectory within few control points. Therefore, although the optimized trajectory execution may be interrupted, the system herein may quickly return to the optimized trajectory based on the calculation and execution of the resumption trajectory.

Some embodiments herein further relate to using at least some of the processes disclosed herein to reduce the delivery time associated with step-and-shoot delivery treatments, without undue sacrifice of delivery accuracy. A characteristic of step-and-shoot treatment deliveries is that the mechanical components remain static during an interval when the beam is on (i.e., during shoot segment). The present disclosure provides a mechanism to generate a trajectory with a reduced delivery time by allowing a gantry, for example, to move within some predefined tolerance during the shoot segments.

In some embodiments, each element of an RTDS that is implicated in a control point, including the radiation output itself, may be considered as a component. The individual discrete positions of each component are prescribed by the treatment plan at the control points. Between each control point, each component moves in a linear or circular path following a "change-cruise-change" velocity profile or model. Yet, a continuous position versus time trajectory of any of the components is not prescribed in the treatment plan. However, for any component and for any segment, the actual trajectory is expected to be close to linear (over time), and the deviation from a linear trajectory is constrained (i.e., limited). There also exist constraints on velocity, acceleration, and jerk specific to each component and at each segment. Accordingly, a goal of some embodiments herein is to generate synchronous trajectories of all the components in such a way that the total delivery time is minimized and all of the constraints are satisfied.

For purposes of some embodiments herein, it is assumed that a radiation treatment plan is described based on the International Electrotechnical Commission (IEC) and Digital Imaging and Communications in Medicine (DICOM) standards, unless otherwise stated. Also, the notations defined in Table 1 below may be used throughout the following discussion.

In some aspects, the following pre-processing steps may be applied to the treatment plan before a trajectory generation process is performed. For any rotating component (e.g., gantry, collimator, etc.), as long as the rotation direction is not reversing, the angle values for the components in the control points are re-expressed in a contiguous monotonic fashion so that an algebraic subtraction of the angle values in consecutive control points reveal the amount of rotation. Also, the treatment plan may only specify the positions of the leaf end points. Multiple combinations of carriage positions and leaf extents that satisfy Equation 1 (described in Table 1 below) may achieve the same position of the leaf end points. Unless a treatment plan explicitly describes the carriage positions, heuristics are used to decompose the positions of the leaf end points into a "suitable" combination of the position of the common carriage and individual leaf extents. This approach facilitates the treatment of the carriages and the leaf extents as separate "components" in the trajectory generation process(es) herein.

A RTDS may have many different moving components that each have individual limits on their position, velocity, acceleration, jerk and other motion parameters. Successful delivery of a radiotherapy plan requires simultaneous movement of these components through a series of configurations. For accurate delivery, the components are (implicitly) expected to travel at somewhat constant velocity between respective successive configurations. To ensure rapid plan delivery, the components are expected to move between configurations as fast as possible without violating any limits/constraints, all the while maintaining synchronous arrival at each control point. These twin objectives may be described below in a formal way, as illustrated in Table 1.

Given the set of mechanical (and dose) components $\Xi$, a treatment plan consisting of M+1 control points (M segments), a velocity model, limits on the velocity, the acceleration and the jerk for each component $\xi \in \Xi$ in each segment $s | 1 \leq s \leq M$, we want to find a sequence of time points $0 = T^0 \leq T^1 \leq \ldots T^M$ such that the total delivery time is minimized while simultaneously satisfying the following constraints (A1, A2, and A3).

For constraint A1, each component moves simultaneously between their respective control point positions while their individual trajectory over time is close to linear trajectory over time. That is, $$\forall \xi, \forall j, 0 \leq j \leq M, \forall t, T^j \leq t \leq T^{j+1},$$

$$\xi(t=T^j)=\xi(CP^j) \text{ and } |\xi(t)-\xi_{linear}(t)| \leq \Delta^\xi \quad (2)$$

TABLE 1

Notations for RTDS components $\theta_G$, $\Theta_{MLC}$, $\Phi_C$, $X_C$, $Y_C$, $Z_C$: the angular position of the RTDS gantry, the multi-leaf collimator (MLC) and the couch, and the lateral, longitudinal and vertical positions of the couch respectively.
$Y_{J1}$, $Y_{J2}$: Position of the Y1 and Y2 jaw beam limiting device (BLD).
$X_{I11}, \ldots, X_{I1N}$, and $X_{I21}, \ldots, X_{I2N}$: Positions of the end points of X1 and X2 leaves of the MLCs as specified in the plan. The MLC leaves are separated in two banks, N leaves in each bank and each bank is connected to a carriage. The positions of the leaf end points are determined by the position of the common carriage and the extent by which the individual leaves extend from the carriage.
$X_{B1}$, $X_{B2}$: Position of the X1 and X2 bank (carriage).
$X_{L11}, \ldots, X_{L1N}$, and $X_{L21}, \ldots, X_{L2N}$: The non-negative extents by which individual leaves protrude from their respective carriages. The leaves connected with the X1 (respectively, X2) carriage can only extend in positive (respectively, negative) X direction in BLD system.
$X_{B1}^{min}$, $X_{B1}^{max}$, $X_{B2}^{min}$, $X_{B2}^{max}$: These are the allowable minimum and maximum position of the X1 and X2 carriages in the BLD co-ordinate system.
$X_{L1}^{min}$, $X_{L1}^{max}$, $X_{L2}^{min}$, $X_{L2}^{max}$: These are the minimum and the maximum (non-negative) extent of the leaves connected to X1 and X2 carriages. The following relationships hold $\forall 1 \leq k \leq N$:
$X_{I1k} = X_{L1k} + X_{B1}$; $X_{L1}^{min} = 0 \leq X_{L1k} \leq X_{L1}^{max}$; $X_{B1}^{min} \leq X_{B1} \leq X_{B1}^{max}$
$X_{I2k} = X_{B2} - X_{L2k}$; $X_{L2}^{min} = 0 \leq X_{L2k} \leq X_{L2}^{max}$; $X_{B2}^{min} \leq X_{B2} \leq X_{B2}^{max}$ (1)
$\mathcal{D}$: The cumulative dose
$\Xi = \{\mathcal{D}, \theta_G, \Theta_{MLC}, Y_{J1}, Y_{J2}, X_{I11}, X_{I12}, \ldots X_{I1N}, X_{I21}, X_{I22}, \ldots X_{I2N}, \Phi_C, X_C, Y_C, Z_C\}$ is the set of all components.
The treatment plan is a sequence of beams. Each beam is a sequence of control points. $CP^j = [\mathcal{D}^j, \theta_G^j, \Theta_{MLC}^j, Y_{J1}^j, Y_{J2}^j, X_{I11}^j, X_{I12}^j, \ldots X_{I1N}^j, X_{I21}^j, X_{I22}^j, \ldots X_{I2N}^j, \Phi_C^j, X_C^j, Y_C^j, Z_C^j]$ is a specification of each component $\xi \in \Xi$ in the j-th control point. A treatment plan is a sequence of M + 1 control points $CP^j$, $0 \leq j \leq M$. In particular, $\mathcal{D}^j$ is the cumulative dose value of control point $CP^j$ such that $\mathcal{D}^j = 0$ and $\mathcal{D}^{j+1} \geq \mathcal{D}^j$. All types of treatments (step-and shoot, dynamic) are captured by the above description. The transitions between the control points are called segments and are numbered by the index s. In a treatment plan of M + 1 control points, there will be M segments where segment s, $1 \leq s \leq M$ is a transition from $CP^{s-1}$ to $CP^s$. $T^0$ denotes the start time of delivery, and $T^j$ denotes the time when the control point $CP^j$ is reached simultaneously by all components.
$\xi(t)$, $\xi(CP^j)$: For each component $\xi$, let $\xi(t)$ denote the position (or cumulative dose in case of the "dose" component) of a component at time t in the generated trajectory. Also let $\xi(CP^j)$ denote the position of the component $\xi$ at control point j as prescribed by the treatment plan.
$V_{max}^{\xi,s}$, $A_{max}^{\xi,s}$, $J_{max}^{\xi,s}$: the absolute limit on velocity, acceleration and jerk, respectively, for any component $\xi$ at the segment s. Due to the effect of gravity, the limits may be different depending on the projection of the gravitational field along the direction of motion. To accommodate this, the constraint limits are segment-dependent.

$$\xi_{linear}(t) := \xi(CP^j) + \frac{(\xi(CP^{j+1}) - \xi(CP^j))}{(T^{j+1} - T^j)} \cdot (t - T^j)$$

denotes the ideal trajectory of each component that is linear over time between successive control point positions. And $\Delta^\xi$ denote the maximum deviation from this ideal linear trajectory (as shown in Figure 2) that may be tolerated for the component $\xi$. This limit is determined during treatment planning.

For constraint A2, all of the components begin (at first control point) and end (at last control point) their trajectories with zero velocities and accelerations. That is, $$\forall \xi, \dot{\xi}(t=T^0)=\ddot{\xi}(t=T^M)=0, \text{ and } \ddot{\xi}(t=T^0)=\ddot{\xi}(t=T^M)=0 \quad (3)$$

For constraint A3, for each component $\xi$ and for each segment s, all the constraints on velocity, acceleration and jerk ($J_{max}^{\xi,s}$), are satisfied:

$$\forall \xi, \forall s, 1 \leq s \leq M, j=s-1, \text{ and } \forall t, T^j \leq t \leq T^{j+1},$$

$$|\dot{\xi}(t)| \leq V_{max}^{\xi,s}, |\ddot{\xi}(t)| \leq A_{max}^{\xi,s}, \text{ and } |\dddot{\xi}(t)| \leq J_{max}^{\xi,s}, \quad (4)$$

where j is the control point index and s is segment index.

In some embodiments, a desired outcome of a trajectory generation herein requires that the total delivery time is minimized while satisfying all of the foregoing constraints. For a segment s between the control points j and j+1, let $h^s = T^s - T^{s-1} = T^{j+1} - T^j$ be the time taken to move all components as planned. Then, the objective is to minimize the total delivery time that can be represented as:

$$T_{del} := \Sigma_{s=1}^M h^s \quad (5)$$

In order to achieve the above aspects, a number of conditions need to exist. One is a process to determine the feasibility of a trajectory that describes the motion of any component between two positions (i.e., control points) in one dimension, in a given duration and with given entry and exit speeds while following a general class of "monotonic change—cruise—monotonic change" velocity models, and satisfying position, velocity, acceleration and jerk limits. Another condition is an optimization process that iteratively allocates durations to each segment, uses the above process to check the feasibility of the allocated durations for each component and each segment, and determines the feasible allocation that results in the minimum total duration.

Figure 3:
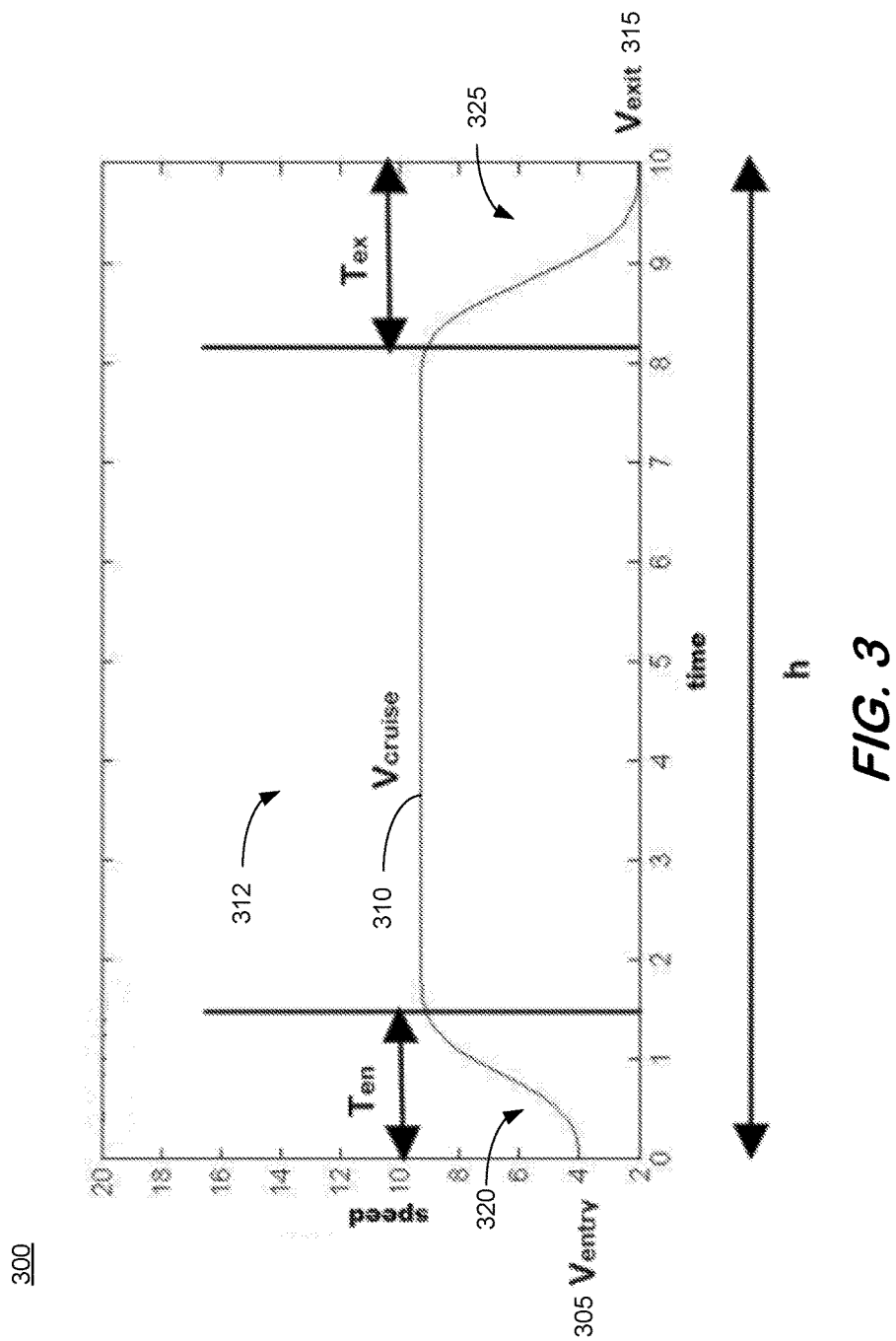
FIG. 3 is an illustrative depiction of a generic class of velocity model, in accordance with some embodiments herein.

Regarding the feasibility of a position trajectory between two points for a generic class of velocity models, a process is undertaken to determine whether a component can traverse a given distance in a given interval while respecting kinematic constraints and following a general class of velocity model involving "monotonic change—cruise—monotonic change" pattern. Such a generic class of velocity model is illustrated in FIG. 3. As shown in FIG. 3, the velocity model 300 exhibits a "monotonic change—cruise—monotonic change" behavior in the form of a monotonic increase in velocity from an entry velocity 305 to a cruise velocity 310, a cruise phase 312, and a monotonic decrease from the cruise velocity 310 to the exit velocity 315. A settling time 320 from the entry velocity to the cruise velocity is shown, as well as a settling time 325 from the cruise velocity to the exit velocity. The total duration, h, is the sum of the two settling times and the time to cruise.

To determine the feasibility of a trajectory for the generic class of velocity model that satisfies the constrains and limits as discussed above, two sub-problems are defined and addressed. In the first, the minimum duration that is required to travel a certain distance under the given kinematic constraints is determined. In the second, a determination is made of whether it is feasible to cover a certain distance within a given duration under the given kinematic constraints, and to calculate the durations of the acceleration, cruise, and declaration phases. A formal description of these problems follows.

It is noted that the feasibility determinations presented herein may be relevant to many applications, of which radiotherapy is just one. While some of the processes disclosed herein are meant for objects moving in a straight line, they may be equally applicable for objects moving in circular trajectories, where the linear position and its derivatives may be respectively replaced by quantities relevant to rotational motion.

In some aspects we can assume an object travels in a straight line from point $P_{entry}$ to point $P_{exit}$. Without any loss of generality let us assume that, along the motion axis, $P_{exit} > P_{entry}$. Given the distance $D = |P_{exit} - P_{entry}|$, monotonic continuous velocity models $f(\bullet)$ and $g(\bullet)$, the allowable maximum absolute speed $V_{max}$, the entry speed $V_{entry} \leq V_{max}$ the exit speed $V_{ex} \leq V_{max}$, the maximum absolute acceleration $A_{max}$, the maximum absolute jerk $J_{max}$ and a position tolerance $\Delta$, we want to find the minimum duration h and its components, namely the entry settling time $T_{en}$, the exit settling time $T_{ex}$, the cruise duration $T_{cruise}$, and the cruise velocity $V_{cruise} \leq V_{max}$, such that the following conditions (1-5) are simultaneously satisfied. Here the entry settling time (respectively the exist settling time) is the time required to change the speed of the component from the entry speed to a cruise speed (respectively from the cruise speed to the exist speed), and cruise speed is the constant speed where the component travels without any acceleration or deceleration.

Per Condition 1, the velocity model of the object follows a monotonic change—cruise—change pattern as shown in FIG. 3 and as expressed below:

$$v(t) := \begin{cases} f(0) = V_{entry}, \dot{f}(0) = 0 & \text{if } t = T_{entry} \\ f(t - T_{entry}) & \text{if } T_{entry} < t < T_{entry} + T_{en} \\ f(T_{en}) = V_{cruise} = g(T_{ex}) \text{ and} \\ \dot{f}(T_{en}) = \dot{g}(T_{ex}) = 0 & \text{if } T_{entry} + T_{en} \leq t \leq T_{exit} - T_{ex} \\ g(T_{exit} - t) & \text{if } T_{exit} - T_{ex} < t < T_{exit} \\ g(0) = V_{exit}, \dot{g}(0) = 0 & \text{if } t = T_{exit} \end{cases} \quad (6)$$

For Condition 2, the total duration is composed of the entry settling time, the cruise time and the exit settling time, as represented below.

$$h = T_{exit} - T_{entry} = T_{en} + T_{cruise} + T_{ex} \quad (7)$$

The Condition 3, states that the limits on the velocity, acceleration and jerk are to be satisfied:

$$|v(t)| \leq V_{max}, |a(t)| = |\dot{v}(t)| \leq A_{max}, \text{ and } |J(t)| = |\ddot{v}(t)| \leq J_{max} \quad (8)$$

Condition 4 states that the prescribed distance D is to be traversed in the duration, as represented below:

$$\int_{T_{entry}}^{T_{entry}+T_{en}} f(t - T_{entry}) dt + V_{cruise} \cdot T_{cruise} + \int_{T_{exit}-T_{ex}}^{T_{exit}} g(T_{exit} - t) dt = D \quad (9)$$

For Condition 5, the deviation of the generated position trajectory from the linear position trajectory over time has to stay within tolerance and is represented as follows:

$$|q(t) - q_{linear}(t)| \leq \Delta \forall t, T_{entry} \leq t \leq T_{exit} \text{ where} \quad (10)$$

$$q(t) := \int_{T_{entry}}^{t} v(t) dt, q_{linear}(t) := \frac{D}{h} \cdot (t - T_{entry})$$

With regards to determining the minimum duration h and its components, three sub-procedures may be used to solve this problem. (1) A determination is made to find out how much settling time is needed to change the velocity of an object from one velocity to another velocity under the given constraints. (2) A determination is made regarding the distance that is traversed during this change in velocity. And, (3) a determination is made regarding the time instant where the generated position trajectory is maximally different from a linear position trajectory.

Regarding sub-procedure 1, given the monotonic velocity model f(•) with known initial velocity and zero initial acceleration (f(0)=$V_i$, f(0)=0), we find the settling time $T_{setting}$ to reach some cruise velocity with zero acceleration (f($T_{settling}$)=$V_f$, f($T_{settling}$)=0). This settling time depends on the specific functional form and parameters of the velocity model. Specific solutions for exponential and double-S velocity models are presented in the Appendix. In general, one finds the time $T_{mid}$ by which the velocity changes from $V_i$ to the mid-velocity $|(V_f+V_i)/2|$ and the acceleration changes from 0 to a maximum value. The maximum value of the acceleration is limited by $A_{max}$, the maximum value of the jerk is limited by $J_{max}$, and whenever the jerk becomes zero when the acceleration reaches the maxima at this mid velocity position. Once this mid-velocity is reached, the acceleration and the jerk follows a symmetric profile until the velocity reaches $V_f$ with zero acceleration. The settling time is computed as $T_{settling}=2T_{mid}$.

For sub-procedure 2, given a velocity model, one can compute the distance traversed, q(t), as the area under the velocity profile, unless an analytic expression is available.

For sub-procedure 3, it is noted that based on the theory of derivatives, when the deviation $|q(t^*)-q_{linear}(t^*)|$ reaches a maximum at some t=t*, the velocity matches the average velocity, i.e., $$v(t^*) := \dot{q}(t^*) = \dot{q}_{linear}(t^*) = \frac{D}{h}.$$

This fact is used to compute t* and $|q(t^*)-q_{linear}(t^*)|$ and to decide whether Condition 5 discussed above is satisfied or not.

Accordingly, a solution regarding the feasibility of a position trajectory between two points for a generic velocity model can be characterized by the following steps.

1. For a feasibility check, one computes the settling time and settling distances to change the velocity from $V_{entry}$ to $V_{exit}$ under the given constraints. If the settling distance is more than the allocated distance D, no valid duration h can be found to solve the problem. Otherwise, the problem may be solved iteratively as described herein.

2. The iteration is initiated by assuming a cruise velocity as $V_{max}$. Then, at each iteration,
   (a) compute $T_{en}$ and $T_{ex}$, as well as the distances traversed during these two phases.
   (b) If the sum of distances is more than the allocated distance, then move to the next iteration with a reduced cruise velocity.
   (c) If the sum of distances is less than or equal to the allocated distance, then compute the cruise time as the ratio of the remaining distance and the cruise velocity.
   (d) As a final check, using Sub-Procedure 3 above, compute the maximum deviation between the generated trajectory and a linear trajectory over time. If the maximum deviation is within tolerance, then one has a solution. Else, move to the next iteration with a reduced cruise velocity.

Regarding the second problem (i.e., the optimization process, Problem 2). It is noted that this problem is similar to Problem 1, except that instead of trying to determine the minimum duration, we want to establish whether a given duration h is feasible while simultaneously satisfying the constraints expressed in Equations 6, 7, 8, 9, and 10 and to find the corresponding values of the entry settling time $T_{en}$, the exit settling time $T_{ex}$, the cruise duration $T_{cruise}$ and the cruise velocity $V_{cruise} \leq V_{max}$ for such a solution.

To address Problem 2, note that a solution herein builds on one additional sub-procedure where the highest and lowest possible cruise velocities that may be attained in the given duration and satisfying all the other kinematic constraints is calculated. This sub-procedure (i.e., Sub-Procedure 4) calculates the highest and the lowest cruise velocities that can be reached for a given allocated duration under the constraints expressed in Equations 6, 7, 8, 9, and 10. Note that the entry settling time is the time to reach some cruise velocity from a given entry velocity and, similarly, the exit settling time is the time to reach the exit velocity from some cruise velocity under similar constraints. The maximum effective cruise velocity $V_{max\_eff}$ is now computed by iteratively checking cruise velocities $V_{max}$ or lower at which the sum of entry and exit settling times becomes just equal to or lower than the allocated duration. Similarly, the minimum effective cruise velocity $V_{min\_eff}$ is computed by iteratively checking cruise velocities equal to or greater than 0 at which the sum of entry and exit settling times becomes just equal to or lower than the allocated duration.

Figure 4:
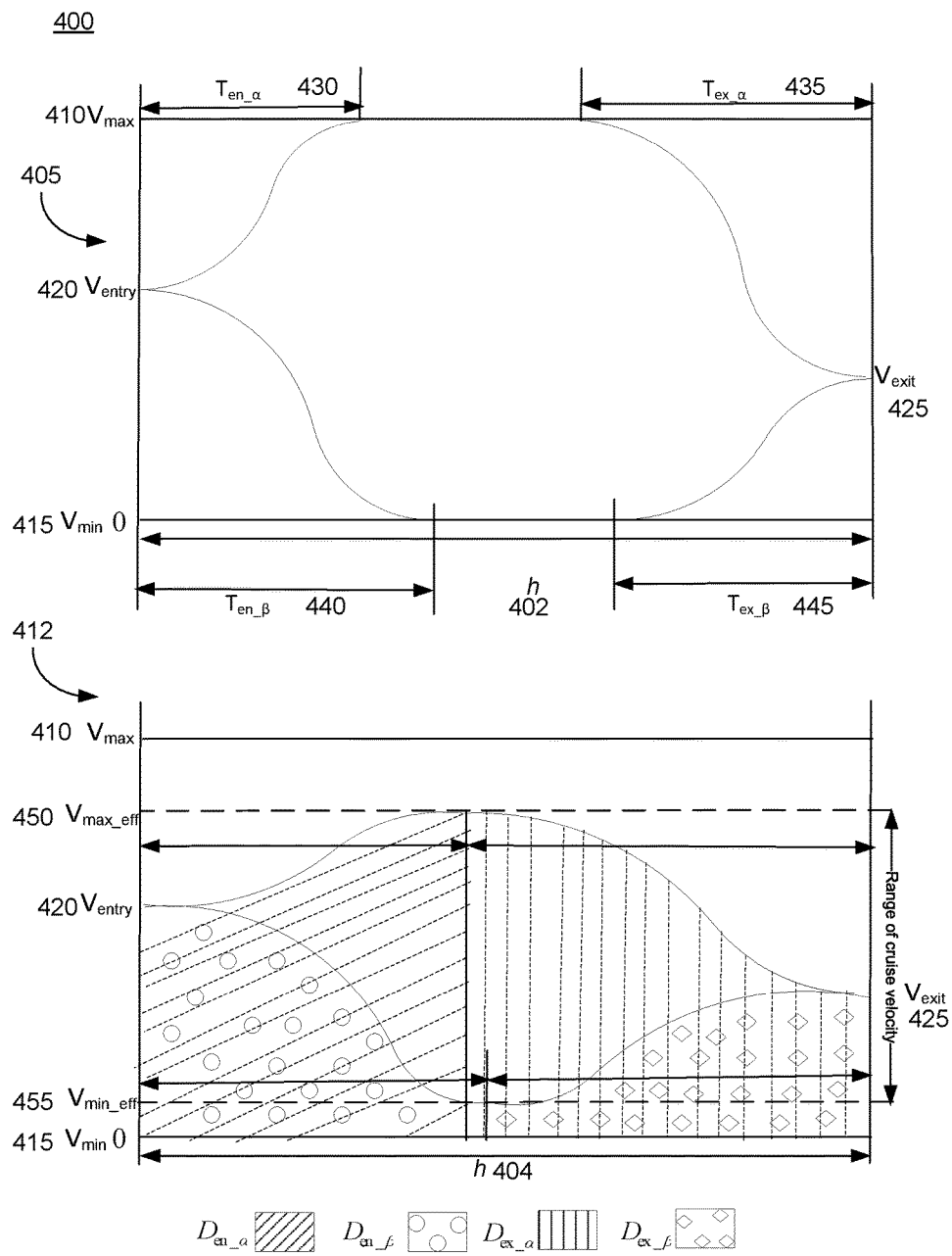
FIG. 4 is an illustrative depiction of a representation of kinematic constraints of components of a radiation delivery system, in accordance with some embodiments.

FIG. 4 graphically illustrates, generally at 400, aspects of the relationships between $V_{entry}$ (420), $V_{exit}$ (425), $V_{max}$, $V_{min}$, the allocated duration, and the corresponding distances. FIG. 4 includes a graphical representation at 405 showing both the maximum velocity $V_{max}$ (410) and the minimum velocity $V_{min}$ (415) of zero may be reached since both the $T_{en\_\alpha}$ (430)+$T_{ex\_\alpha}$ (435) and $T_{en\_\beta}$ (440)+$T_{ex\_\beta}$ (445) are less than the allocated duration h (402).

In the lower graph of FIG. 4 at 412, $V_{max\_eff}$ (450)≤$V_{max}$ (410) is the maximum effective cruise velocity that allows $T_{en\_\alpha}+T_{ex\_\alpha}$=h. Similarly, $V_{min\_eff}$ (455)≥0 ($V_{min}$, 415) is the minimum effective cruise velocity for which $T_{en\_\beta}+T_{ex\_\beta}$=h (404). The distances traversed are computed as the area under the velocity profiles. Here, $D_{max}=D_{en\_\alpha}+D_{ex\_\alpha}$ and $D_{min}=D_{en\_\beta}+D_{ex\_\beta}$ are the maximum and the minimum distances, respectively, that may be traversed in the allocated duration with all constraints satisfied.

Further regarding a solution to Problem 2, we herein determine, iteratively, a cruise velocity between $V_{min\_eff}$ and $V_{max\_eff}$ such that not only does the sum of the entry time, exit time, and cruise time equal the allocated duration, but also the sum of the traversed distance in these phases equals the allocated distance between the two points. Referring to FIG. 4 again, the traversed distance at any phase is expressed as the area under the velocity-time graph and the solution further includes and/or considers the following:

1. Computing the settling distances ($D_{en\_\alpha}$, $D_{ex\_\alpha}$) to the maximum effective cruise velocity and the settling distances ($D_{en\_\beta}$, $D_{ex\_\beta}$) to the minimum effective cruise velocity.

2. The maximum distance that may be traversed within the allocated duration while reaching the maximum effective cruise velocity from the given entry velocity and reaching the given exit velocity from the maximum effective cruise velocity is the area under the velocity graph and may be expressed as $D_{max}=D_{en\_\alpha}+D_{ex\_\alpha}+D_{cruise\_\alpha}$ where $D_{cruise\_\alpha}=$ (h−($T_{en\_\alpha}+T_{ex\_\alpha}$))·$V_{max\_eff}$.

3. The minimum distance that may be required to be traversed within the allocated duration while reaching the minimum effective cruise velocity from the given entry velocity and reaching the given exit velocity from the minimum effective cruise velocity is the area under the velocity graph and may be expressed as $D_{min}=D_{en\_\beta}+D_{ex\_\beta}+D_{cruise\_\beta}$ where $D_{cruise\_\beta}=(h-(T_{en\_\beta}+T_e))·V_{min\_eff}$.

4. If D is the allocated distance and $D > D_{max}$, then the allocated duration is not feasible as the distance to be traveled is larger than the maximum that can be traveled under the constraints.

5. And, if $D < D_{min}$, then the allocated duration is not feasible as the distance to be traveled is smaller than the minimum that can be traveled under the constraints.

6. If $D_{min} \le D \le D_{max}$, we iteratively reduce the cruise velocity from $V_{max\_eff}$ to $V_{min\_eff}$ until a cruise velocity $V_{cruise}$ and corresponding velocity profile v(t) are found for which the distance traveled [area under v(t)] matches D.

7. As a final check for feasibility, a computation is made for the time instants t=t* where v(t*)=D/h and determine the maximum departure as $|q(t^*) - q_{linear}(t^*)|$. If it is less than $\Delta$, the allocated duration is feasible under the constraints.

In preparation for optimization, we compute a lower bound and an upper bound on the duration for every segment.

For the computation of the lower bound, we assume each component is moving with maximum possible velocity and then the slowest (longest) duration is considered as the lower bound.

$$\forall s, j, 1 \le s \le M, j = s - 1 \quad (11)$$

$$h^{s\_min} := \max_{\forall \xi} \frac{|\xi(CP^{j+1}) - \xi(CP^j)|}{V_{max}^{\xi,s}}$$

For the computation of the upper bound, it is assumed that every component stops at each control point. With this assumption, for a given velocity model, we determine the minimum duration for any component to traverse a segment while satisfying all constraints. The upper duration bound for the segment is obtained by determining the maximum of these minimum durations. That is, $\forall s, j, 1 \le s \le M, j = s - 1$ compute, $$h^{s\_max} := \max_{\forall \xi} findMinDuration(f(\cdot), \quad (12)$$
$$g(\cdot), \xi(CP^j), \xi(CP^{j+1}), 0, 0, V_{max}^{\xi,s}, A_{max}^{\xi,s}, J_{max}^{\xi,s}, \Delta^{\xi})$$

FIG. 5 is a flow diagram of process 500 according to some embodiments. Process 500 and the other processes described herein may be performed using any suitable combination of hardware devices and software implementations of components, devices, and systems. Software embodying these processes may be stored by any tangible, non-transitory medium, including but not limited to a hard disk drive, a solid-state drive, a CD-ROM, a DVD-ROM, a flash drive, optical storage, and other types of storage devices. The process of FIG. 5 may be implemented, in some embodiments, by at least some of the elements of system 100, yet embodiments are not limited thereto.

At operation 505, a plurality of one-dimensional positions as defined in a radiotherapy treatment plan are obtained. The plurality of one-dimensional positions are also referred to as control points. FIG. 2 introduced hereinabove may be referenced again regarding the plurality of one-dimensional positions.

At operation 510, a set of position related constraints for a plurality of mechanical and radiation producing components of a radiation treatment delivery system (e.g., 100) for delivering a radiotherapy treatment plan by synchronous motion of the plurality of mechanical and radiation producing components traversing a prescribed sequence of the plurality of positions in a predetermined time is obtained. Referring to FIG. 100, the plurality of mechanical and radiation producing components may include, for example, gantry 115 and radiation beam shaping components therein. In accordance with aspects of the present disclosure, all of the all of the kinematic constraints for each of the plurality of mechanical and radiation producing components are obtained and used in some embodiments herein. In some instances, the set of position related constraints for the plurality of mechanical and radiation producing components may be included in a record or set of records including, at least in part, a radiotherapy treatment plan.

Process 500 proceeds to operation 515 where a determination is made regarding a trajectory and a minimum duration for the radiation treatment delivery system to traverse the prescribed sequence of the plurality of positions and deliver the radiotherapy treatment plan. The trajectory and minimum duration determined at operation 515 are calculated while adhering to (i.e., satisfying) the constraints of each of the plurality of mechanical and radiation producing components and, further being within a predetermined tolerance limit of a linear trajectory along the prescribed sequence of the plurality of positions. In some embodiments, operation 515 may include iterative process(es) in order to reach a final determination of the trajectory and minimum duration determined that satisfy the constraints of each of the plurality of mechanical and radiation producing components, including being within a predetermined tolerance limit of a linear trajectory along the prescribed sequence of the plurality of positions.

At operation 520, the plurality of mechanical and radiation producing components of the radiation treatment delivery system may be controlled (i.e., operated) to execute the determined trajectory within the determined minimum duration. In this manner, the radiation treatment delivery system may delivery radiation per the radiotherapy treatment plan with the optimized trajectory in a minimum amount of time.

In some embodiments, an optimization process herein may be executed in an iterative manner, including for example, the following iterative loop:

1. Allocate a duration to each segment, bounded by the lower and upper bounds. Allocation can begin by allocating shorter durations, closer to the lower bound.

2. An average velocity of each component for each segment is calculated by dividing the distance to be traversed by the component for that segment with the allocated duration of the segment.

3. The transition velocity of each component at each control point is calculated as the mean of its average velocities in the neighboring segments. This determines the entry and exit velocity of each component in each segment. In some embodiments, either the harmonic mean, arithmetic mean, or some other mid values of the average velocities of the neighboring segments as the transition velocity may be used. In general, when an object travels the same distances with different speeds, its average speed is the harmonic mean of the individual speeds. Alternately, if the object travels the same duration with different speeds, its average speed is the arithmetic mean of the individual speeds. However, if the component reverses direction at a control point (non-monotonic), we assign transition velocity as 0.

4. The feasibility of the duration of a segment is determined by determining whether the duration is feasible for every component with the allocated entry and exit velocities, while satisfying all constraints.

5. If feasibility is satisfied for all segments, then a solution is determined. Otherwise, the duration of the segment is incremented for the failed feasibility and the process is repeated (iteratively) in search of a feasible solution.

In some instances, when an optimized trajectory is downloaded or otherwise provided to a linac, it may be the case that the treatment is interrupted for some reason. The point of interruption will match with some point on the optimized trajectory in terms of position of all the components. However, if the treatment is resumed from that interruption point, the trajectory will not match the optimized trajectory in terms of velocity since all of the components will have to resume movement with a zero velocity. Therefore, it is not guaranteed that all of the components will reach the next control point with respective velocities as computed in the determining of the optimized trajectory.

However, instead of a determining a completely new trajectory optimization, the present disclosure includes a process to generate a resumption trajectory to quickly catch up with the pre-computed (i.e., already determined) optimized trajectory within a few control points both in terms of position and velocity.

A key aspect for the fast performance of such a process is that instead of using the complete "remaining" trajectory plan as an input to the optimization process, we use incremental mini-plans as input. Such mini-plans include the point of resumption as the first control point and a subsequent few planned control points. Also, for the last control point of such a mini-plan, the components are expected to match the corresponding control point in the optimized trajectory both in terms of position and velocity. Therefore, once there is a solution to the optimization problem for the mini-plan, it can be appended to the remaining part of the pre-computed optimized trajectory to get an overall optimized solution for resumption. Herein below, is an informal description of the solution.

In some embodiments, it can be assumed that the treatment interruption takes place between $CP^{u-1}$ and $CP^u$. Without any loss of generality we can assume that the radiation was on between these two CPs. Otherwise, one can run the resumption algorithm beginning with $CP^u$ assuming that the linac will be setup before resumption in a way that the positions of all the components match that of $CP^u$. Also let $\mathcal{D}_{int}$, $\mathcal{D}^{u-1} < \mathcal{D}_{int} < \mathcal{D}^u$ be the cumulative dose at the time of interruption.

The first control point of the mini-plan, namely $CP_{min}^0$, will be constructed with a dose value equal to the cumulative dose at interruption. The position of the other mechanical components will be determined by their respective prorated value.

Given these assumptions and constraints, an iterative loop of mini-plans are constructed with incremental numbers of control points. In the first iteration, the mini-plan consists of two control points. The first control point corresponding to the state of the components at the time of interruption. The second is the next control point in the original plan. In general, at every iteration, a mini-plan is constructed that includes one more (compared to the number of CPs in the last iteration) control points from the original plan. (1) The newly added control point becomes the last control point of the mini-plan of the current iteration. Unlike the original plan, the last control point is not static for the mini-plan. Instead, the velocity of all the components in the last control point of the mini-plan should match the velocity of the components at the corresponding control point in the optimized trajectory. (2) An optimization is applied to the mini-plan.

The optimization of the mini-plan differs from the optimization of the overall plan in the following ways. (i) Unlike the original plan, in the last control point of the mini-plan, the components may not be static. However, for the intermediate control points of the mini-plan the transition velocities are computed in the same way as is done in the original optimization algorithm. Namely, as the arithmetic or harmonic mean of the average velocities in the neighboring segments, which in turn depend on the allocated durations. (ii) The lower bound on the duration of the segments of the mini-plan is equal to the duration of the corresponding segments in the optimized trajectory. However, for the first segment of the mini-plan, the lower bound of the duration is equal to the remaining planned duration (computed in proportion to remaining planned dose) of the interrupted segment. (iii) The upper bound of the duration of the segments of the mini-plan is equal to the upper bound on the duration of the corresponding segments in the optimized trajectory. However, for the first segment of the mini-plan, the upper bound is computed as a fraction of the original upper bound in proportion to remaining planned dose of the interrupted segment. (iv) The optimization of the mini-plan will attempt far fewer trials than the full optimization. This is because, for the last control point of the mini-plan, if the planned velocity of all the components cannot be achieved within a few trials, then the optimization loop enters a new iteration and adds one more control point from the original plan into the mini plan and re-attempts optimization.

In some aspects, if a feasible allocation of durations of the segments of the mini-plan is found within the limited number of attempts, then the resumption trajectory process exits with a status of "success". If a feasible allocation was not found and the last control point of the mini-plan is not the last control point of the original plan, then repeat the loop. That is, the current mini-plan is augmented with another control point from the optimized trajectory. As in the previous iteration, for this last control point, each component is not necessarily static and is specified with the same position and velocity it held in the corresponding control point in the original plan. If a feasible allocation was not found and the last control point of the mini-plan is also the last control point of the original plan, then the mini-plan is now treated as a full plan and a solution is obtained with large number of trials, and the worst case upper bound duration of every segment is considered.

It is noted that a large number of external beam radiotherapy treatment plans are step-and-shoot treatment plans with alternating step-and-shoot segments. In a step segment the linac components move to prescribed positions while the dose is switched off. In the shoot segments, the dose is delivered and the linac components maintain their prescribed positions. Delivery of such treatment plans generally takes longer since each linac component comes to a complete stop at the beginning of a shoot segment and starts again with a zero velocity at the beginning of the subsequent step segment.

However, dose calculation in the planning system shows that the delivered dose to the organs may be insensitive to the departure of some of the linac components from their prescribed positions in the shoot segments, as long as such departures are within some prescribed tolerance. The tolerance that can be used for allowing some components to move during the shoot segment is different for different types of components. For example, for leaves, the tolerance will be quite small, but for gantry angle or other rotational components, a larger tolerance may be possible. Such tolerances need to be decided by the planning system. Herein, we disclose a process that reduces the delivery time by exploiting such positional tolerance(s) while respecting constraints on the maximum velocity, maximum acceleration and maximum jerk of all components.

Figure 6:
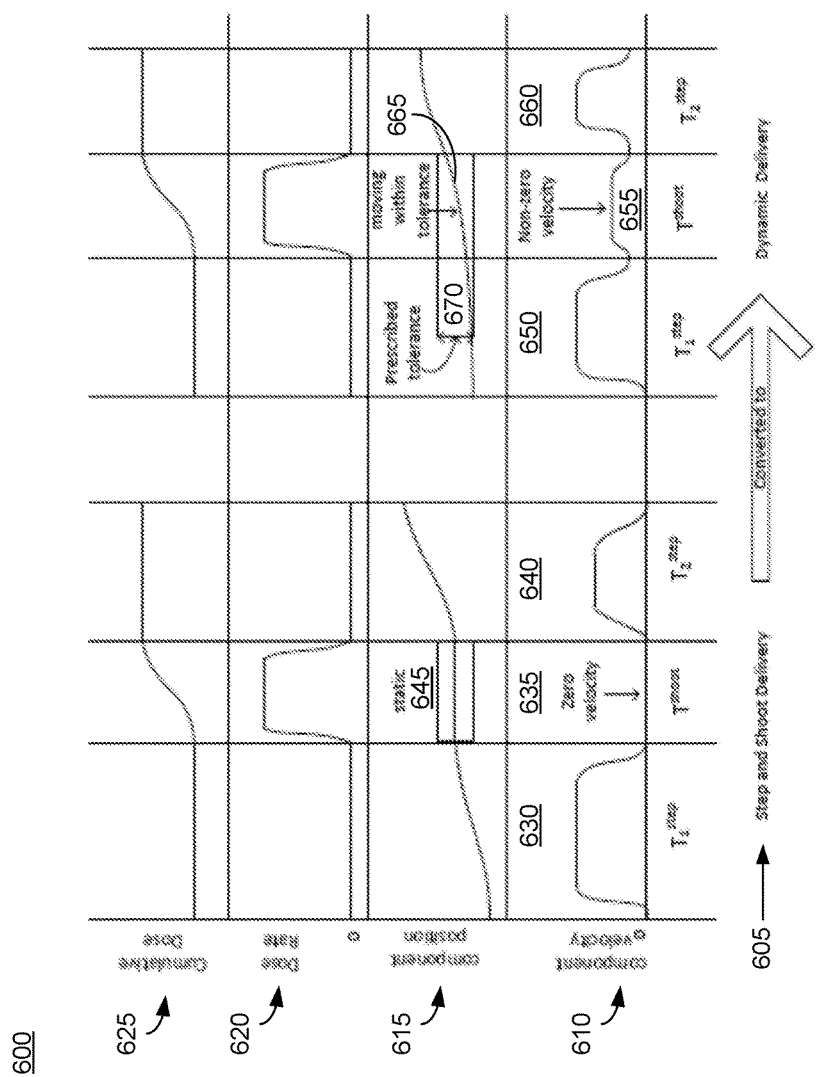
FIG. 6 is an illustrative depiction of some aspects of a step-and-shoot treatment plan, in accordance with some embodiments.

The underlying idea is as follows. A shoot segment is considered monotonic in some component provided the component is not planned to change its direction of movement in the immediately next step segment. If a shoot segment is monotonic in some component, we may allow such component to move in the shoot segment (within tolerance of course) in its monotonic direction without worrying about the possibility that in the immediate next step segment the component will have to change its direction of movement. Allowing such movement ensures that the component need not come to a complete stop at the beginning of a shoot segment. This aspect of a step-and-shoot treatment plan may reduce the distance to travel for that component in the previous and the next step segment. In turn, the duration of these step segments may be reduced, provided the component in question was the slowest component in the step segments. The principle is illustrated in FIG. 6. The duration for the shoot segments however does not change as they are determined by the dose to be delivered, maximum dose rate, etc. A more formal description now follows.

Referring to FIG. 6, a graphical presentation 600 shows the underlying principle for converting step-and-shoot deliveries to dynamic deliveries (605), in accordance with some aspects herein. Graphic 600 includes illustrative graphs of the component velocity 610, component position 615, dose rate 620, and cumulative dose 625. As shown, in a shoot segment (e.g., 655) some delivery system components may enter and exit with non-zero velocity and the components are allowed to move 665 within a specified tolerance 670 from the original prescription. The reduction in delivery time is due to the fact that during the step segments (e.g., 650, 660), components do not necessarily start and end with zero velocities and therefore need to travel smaller distances. It is noted that at least some of the shoot segments (e.g., 635) may have a component velocity of zero for all of the components, as shown by the static positioning of the component(s) at 645 where the surrounding step segments 630 and 640 have entering and exiting velocities of zero.

Using the notations introduced hereinabove, a step-and-shoot treatment is a treatment plan including the following properties. The treatment contains alternate step-and-shoot segments. In a shoot segment s between control point s and s−1, only the dose changes and the mechanical components are static, i.e., $\forall \xi$, $\xi$ other than dose component $\mathcal{D}$, $\xi(CP^s)=\xi(CP^{s-1})$. And in a step segment, s' between control point s' and s'−1, no dose is delivered. That is, $\mathcal{D}(CP^{s'-1})=\mathcal{D}(CP^{s'})$.

The first segment and the last segment is a shoot segment and each even number of segment is a step segment. Therefore, the total number of segments M is odd and the total number of control point M+1 is even.

Also, let s be a shoot segment between control points $CP^s$ and $CP^{s-1}$ and the prescribed position of some component e in this segment is $\xi^*(CP^s)=\xi^*(CP^{s-1})=:\xi^{*s}$. The segment s is considered monotonic for component $\xi^*$ if one of the following cases is satisfied:

$$\xi^*(CP^{s-2}) > \xi^*(CP^{s-1}) =: \xi^{*s} := \xi^*(CP^s) > \xi^*(CP^{s+1}) \text{ or}$$

$$\xi^*(CP^{s-2}) < \xi^*(CP^{s-1}) =: \xi^{*s} := \xi^*(CP^s) < \xi^*(CP^{s+1}) \quad (13)$$

Clearly, we may attempt to use the position tolerance of the component $\xi^*$ in the shoot segment in order to reduce the delivery distance of $\xi^*$ in the neighboring step segments and in effect reduce the duration of the step segments provided (a) $\xi^*$ is the slowest component in the neighboring step segment and (b) the shoot segment is monotonic in $\xi^*$.

In order to avoid any bias error, while converting a shoot segment into a dynamic segment (where the component moves while the dose is on), we want the trajectory of the component $\xi^*$ to be equally distributed around the prescribed position $\xi^{*s}$ in the shoot segment and within the prescribed tolerance $\Delta^{\xi*}$. Two choices are possible. Among the two choices provided by the conversion, the one that "extends" the position monotonicity of the component $\xi^*$ from the neighboring step segment into a "modified" shoot segment is used. In particular, if monotonicity is determined using the first case of the Equation 13 (alternatively the second case) in the original step-and-shoot treatment, then the converted dynamic treatment should satisfy the first case of the Equation 14 (respectively the second case) as shown here.

$$\xi^*(T^{s-1})=\xi^{*s}+\delta^{\xi*s} \text{ and } \xi^*(T^s)=\xi^{*s}-\delta^{\xi*s}$$

$$\text{Or } \xi^*(T^{s-1})=\xi^{*s}-\delta^{\xi*s} \text{ and } \xi^*(T^s)=\xi^{*s}-\delta^{\xi*s} \quad (14)$$

In some embodiments herein, for both practical and computational reasons, only one mechanical component $\xi^*$ (e.g., the gantry) is allowed to move, within tolerance, in the shoot segment.

Regarding the trajectory generation for step-and-shoot treatments with a shorter delivery time, we consider a step-and-shoot treatment plan consisting of M+1 control points, a velocity, acceleration and jerk for each component in each segment s, $1 \leq s \leq M$ and a component $\xi^*$ that is allowed to move in the shoot segment within a maximum position tolerance $\Delta^{\xi*}$ from its planned fixed value in the shoot segment, we want to find a sequence of time points $0=T^0 \leq T^1 \leq \ldots T^M$ such that the following constraints (B1, B2, B3, B4, and B5) are simultaneously satisfied.

For constraint B1, all the components start with a zero velocity and acceleration at the first control point and terminate similarly at the last control point.

$$\forall \xi \dot{\xi}(t=T^0)=\dot{\xi}(t=T^M)=0$$

$$\forall \xi \ddot{\xi}(t=T^0)=\ddot{\xi}(t=T^M)=0 \quad (15)$$

For constraint B2, each of the mechanical (i.e., non-Dose) components (except $\xi^*$) enter and exit each segment with zero velocity and remain static in the shoot segment. Note that segment numbers begin with 1, therefore the odd segments are shoot segments and the even segments are step segments.

$$\forall \xi, \xi \neq \xi^*, \xi \neq \mathcal{D}, \forall j, 0 \leq j \leq M, \xi(t=T^j)=\xi(CP^j), \dot{\xi}(t=T^j)=0$$
and $$\text{odd } s, 1 \leq s \leq M, \forall t, T^{s-1} \leq t \leq T^s, \xi(CP^{s-1})=\xi(t)=(CP^s), \dot{\xi}=0 \quad (15)$$

Regarding constraint B3, the trajectory for the mechanical component $\xi^*$ should be such that its position will be symmetrically distributed on both side of the prescribed position of the component in any shoot segment and will be within the position tolerance of the component. That is, $\forall$ odd $s, 1 \leq s \leq M, \forall t, T^{s-1} \leq t \leq T^s, \xi^*(t)$ is symmetrically disctributed around $\xi^{*s}$ and $|\xi^*(t) - \xi^*s| \leq \Delta^{\xi*}$
where $\xi^{*s}:=(CP^{s-1})=\xi(CP^s)$. (17)

Constraint B4 states that the dose is delivered only in the shoot segments and the cumulative dose is constant at step (even) segments. That is, $\forall j, 0 \leq j \leq M, \mathcal{D}_{(t=T^j)} = \mathcal{D}(CP^j), \dot{\mathcal{D}}_{(t=T^j)} = 0$ and $\forall$ even $s, 1 \leq s \leq M, T^{s-1} \leq t \leq T^s, \mathcal{D}(CP^{s-1}) = \mathcal{D}(t) =$ $\mathcal{D}(CP^s), \dot{\mathcal{D}}_{(t)} = 0$ (18)

Constraint B5 states that, as in the original optimization goal, for each component ξ and for each segment s, all the constraints on velocity ($V_{max}^{\xi,s}$), acceleration ($\lambda_{max}^{\xi,s}$) and jerk ($J_{max}^{\xi,s}$) are satisfied. That is, $$\left\{ \begin{array}{l} \forall \xi \, \forall s, 1 \leq s \leq M, j = s-1, \forall t, T^j \leq t \leq T^{j+1} \\ |\dot{\xi}(t)| \leq V_{max}^{\xi,s}, |\ddot{\xi}(t)| \leq A_{max}^{\xi,s}, |\dddot{\xi}(t)| \leq J_{max}^{\xi,s} \end{array} \right\} \quad (19)$$

It is noted that in some embodiments, an objective is to minimize the total delivery time $T_{del}$ where $h^s = T^s - T^{s-1} = T^{j+1} - T^j$ and $$T_{del} := \sum_{s=1}^{M} h^s.$$

In some embodiments, the goals mentioned hereinabove involve the following operations.

The duration of each shoot segment is solely determined by the amount of dose to be delivered and associated constraints on maximum dose rate, rate of change of dose rate (i.e., "dose acceleration"). It may be assumed a double-S profile for dose as well. Therefore, we can determine the duration of each shoot segment analytically as has been described mathematically.

Next, a relationship between the entry (and the exit) velocity of the component and the amount of tolerance position $\delta^{\xi^*,s} \leq \Delta^{\xi^*}$ it traverses, is established. The relationship is obtained under the constraint that the component ξ* enters and exits the shoot segment s with identical velocity and moves symmetrically in the shoot segment on both sides of the prescribed position while staying within prescribed tolerance $\Delta^{\xi^*}$. Accordingly, the constraints on the maximum velocity and the maximum acceleration of the component in the segment is also respected.

Next, in every step segment the slowest and the second slowest moving components ($\xi_{slowest}^s, \xi_{second\,slowest}^s$) and the corresponding durations ($h_{slowest}^s, h_{second\,slowest}^s$) are identified. For every step segment of the plan and for each mechanical component, we compute the minimum duration to traverse the segment under constraints and with zero entry and exit velocity. Then, for each step segment, the maximum duration (and the slowest component) and second maximum duration (and the second slowest component) is identified as described here.

$h^{\xi,s} = findMinDuration(f(\cdot), g(\cdot),$ (20)

$\xi(CP^{s-1}), \xi(CP^s), 0, 0, V_{max}^{\xi,s}, A_{max}^{\xi,s}, J_{max}^{\xi,s}, \Delta^\xi)$ $\xi_{slowest}^s = \underset{\xi \in \Xi}{\operatorname{argmax}} h^{\xi,s}.$ $h_{slowest}^s = \underset{\xi \in \Xi}{\max} h^{\xi,s}.$ $h_{second\_slowest}^s = \underset{\xi \in \Xi - \{\xi_{slowest}^s\}}{\max} h^{\xi,s}.$ The reason we identify the slowest and the second slowest components in the step segments is because if the segment s+1 is a shoot segment and if in the neighboring segments s and S+2, the slowest moving component is ξ*, i.e., $\xi_{slowest}^s = \xi_{slowest}^{s+2} = \xi^*$, then there is the potential opportunity to reduce the duration of the step segments s and similarly for the step segment s+2 by using the tolerance of the component ξ* in the shoot segment s+1 as illustrated in FIG. 6. The maximum reduction for the step segment s is limited by an amount $h_{slowest}^s - h_{second\,slowest}^s$.

We also develop an iterative procedure to try out combinations of reduced durations in the step segment s and increased use of position tolerance in the shoot segment s+1 to check for a feasible profile for the component ξ. This procedure is repeated for every neighboring step-and-shoot segment pair. Ultimately, a feasible combination is found for the component ξ* such that the duration for the step segment s is reduced and the corresponding entry/exit velocity and position of the component is found in the shoot segment s+1, and the same reduced duration of the step segment s is used to generate a position profile for all other components in that step segment.

To test some of the trajectory generation processes disclosed herein, Applicant used a RapidArc plan for a Varian system and employed the published constraints for the Varian TrueBeam linac with 120 leaf MLC. The plan consists of 177 control points (176 segments) and outputs 385.79 MU. The mechanical constraints applied appear in Table 2. For the RapidArc plan with an exponential velocity model, the total optimized duration was computed to be 128 s. With the double-S velocity model, where longer duration is spent in maximum acceleration, the total duration was calculated as 98 s. The latter value is quite comparable to the average reported duration (126 s) of RapidArc plans. It is noted that that a simulation (e.g., a MATLAB (R2007) implementation) of the optimized trajectory generation was executed in 70.8 s running on an Intel i7-3740QM 2.7 GHz computer with 8 GB of RAM.

TABLE 2

| Mechanical constraints used for trajectory generation | | | |
|---|---|---|---|
| Max gantry speed | 6°/s | Max gantry acceleration | 1.8°/s2 |
| Max leaf speed | 25 mm/s | Max leaf acceleration | 520 mm/s2 |
| Max carriage speed | 15 mm/s | Max carriage acceleration | 250 mm/s2 |
| Max Jaw speed | 50 mm/s | Max Jaw acceleration | 520 mm/s2 |
| Max Dose Rate | 10 MU/s | Max Dose acceleration | 500 MU/s2 |

For the same rapid arc plan, an interruption was simulated between the 164th and 165th control point, the interruption occurring after delivery of 70% of the planned segment dose of the 164th segment. For all other mechanical components (gantry, leaves, jaws), the position at the point of interruption was computed by the same proportion of the segment dose delivered to the total segment dose. An initial mini plan was constructed and the process for the resumption trajectory generation was executed. The resumption process used, at most, 50 trials for each mini plan while trying to match the velocity of each component in the final control point of the mini plan with the corresponding values in the original (optimized) trajectory. If such a match was not found, then the mini plan was extended by another control point from the original plan. For the interrupted RapidArc plan, the resumption process was able to match, within 4 control points from the point of resumption, the velocity of all components with the corresponding values in the original trajectory. It is noted that that a simulation (e.g., a MATLAB (R2007) implementation of the resumption process took 3.16 s to run on the same PC (i.e., Intel i7-3740QM 2.7 GHz computer with 8 GB of RAM) mentioned above.

Figure 7:
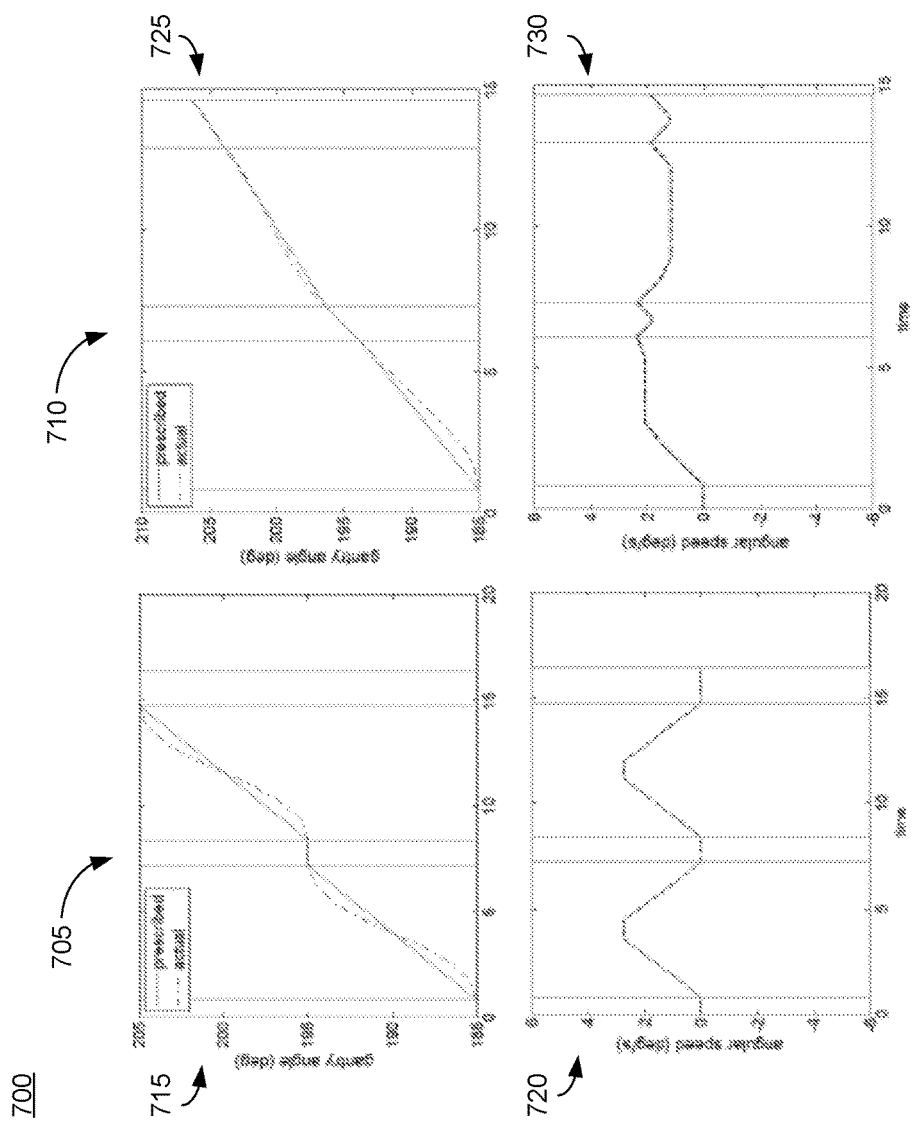
FIG. 7 is an illustrative depiction of a position and velocity profiles, according to some embodiments herein

In some embodiments, in order to evaluate the conversion of a step-and-shoot plan into a dynamic plan, we began with a Siemens' Modulated Arc (mARC) dynamic plan. Siemens' mARC plans are rotational IMRT (rIMRT) plans meant for burst delivery with high dose rate. They differ from Varian's or Electa's VMAT plan in the sense that the dose is not delivered while MLC leaves are moving. Instead, dose is delivered in bursts over very short arc angles and only after an MLC segment shape is formed and verified. They are dynamic plans in the sense that the gantry moves over short arc during dose delivery. Such an rIMRT plan can be easily converted into a step-and-shoot realization by "squeezing" the gantry spread of each shoot segment into the middle of the allowed beam-on angular window, as is the original intention of these rIMRT plans. The resultant step-and-shoot plan consists of 71 segments. In the step-and-shoot delivery, at the beginning of each step segment, every component initiates motion with a zero velocity and comes to a complete stop at the end of each step segment. In the shoot segment, only the dose is allowed to change. In a simulation by Applicant, the constraints shown in Table 2 were used, with the exception that for gantry rotation a maximum gantry acceleration of $1°/s^2$ was used. For the step-and-shoot delivery, the trajectory generation process herein a total delivery time of 276.47 s was determined. As part of the conversion to dynamic segments, the gantry is allowed to move within tolerance in the shoot segments. That is, the gantry component was considered as the component $\xi^*$ that is allowed to move in the shoot segment and a maximum tolerance value of $\Delta^{\xi^*}=1.25$ was allowed in the shoot segment. Consequently, the gantry never comes to a complete stop. The modified delivery scheme realized a delivery time of 236.18 s, a reduction of 15%. An illustrative plot of the gantry position and the velocity for few segments is shown in FIG. 7. FIG. 7 shows the position and velocity profiles for a gantry for a first few segments during a step-and-shoot delivery in the graphs at 705, including graphs for the gantry angle at 715 and the angular speed at 720. Graphs showing, for the dynamic delivery determined in accordance with some embodiments, are shown at 710, including individual graphs for the gantry angle at 725 and the angular speed at 730.

It is reiterated that the processes and sub-procedures herein are developed, at least in part, for the general class of "monotonic change—cruise—monotonic change" velocity models. Among the sub-procedures, an important task is to find the settling time required to change from one velocity to another while respecting the acceleration and jerk constraints. While analytical solutions are possible for double-S and exponential velocity models, iterative numerical procedures may be used for generic velocity models. For most industrial manipulators, velocity models such as trapezoidal, double-S and 15-segment suffice. In these cases, the settling time may be obtained analytically. However, some of the processes disclosed herein to determine a suitable cruise velocity to match the allocated distance with the allocated duration are iterative in nature.

In the optimization process associated with some of the embodiments discussed herein, the segment durations are the independent variables. The entry and the exit velocities of the different components at the control points can also be treated as independent variables. Instead, transition velocities were chosen as either the arithmetic or the harmonic mean of the average velocities of neighboring segments. Such a choice is pragmatic and also avoids highly computationally expense. Moreover, during the optimization process, even the segment durations have not been chosen in a completely random fashion. Instead, each segment durations is initialized with a value a little larger than $h^{s\_min}$ and is increased slowly in cases where feasibility cannot be achieved.

It is noted that a main contribution of the present disclosure is to provide an approach that works for a generic class of velocity models and that also respects positional tolerance constraints between via points. Moreover, while radiotherapy has primarily been the context or field of application chosen for this disclosure, the processes disclosed herein are suitable for any kind of industrial application involving synchronous movement of multiple components.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method implemented on a computing device having at least one processor and a storage device storing a set of instructions for controlling a system operatively connected to the computing device, comprising:
   obtaining, by the at least one processor, a plurality of positions for multiple components of the system defined by a plan;
   obtaining, by the at least one processor, a set of constraints that express limitations for the multiple components at the plurality of positions, the constraints being applicable to the plan where the multiple components synchronously change their positions with time to traverse a prescribed sequence of the plurality of positions, at least one of the multiple components being further constrained to change its position over time by staying within a predefined tolerance to a predefined smooth function of position over time between different positions;
   determining, by the at least one processor, a trajectory of position and a minimum duration in which the multiple components completely synchronously traverse the prescribed sequence of positions while satisfying the constraints for the multiple components;
   generating, by the at least one processor, a record of the determined trajectory of position and the minimum duration for the multiple components; and
   controlling, by the at least one processor, the multiple components of the system to execute, in synchronous motion, the determined trajectory within the determined minimum duration.

2. The method of claim 1, wherein at least one of the plurality of positions is defined in the plan by position like variables.

3. The method of claim 1, wherein the plan comprises an imaging plan and the multiple components include moveable components of an imaging system.

4. The method of claim 1, wherein a pattern for a rate of change of position over time for the multiple components to traverse consecutive positions is one of (i) acceleration, constant velocity, and deceleration, and (ii) deceleration, constant velocity, and acceleration.

5. The method of claim 1, wherein each of the multiple components are constrained to change their position over time by staying within the predefined tolerance to the predefined smooth function of position over time between different positions.

6. A method implemented on a computing device having at least one processor and a storage device storing a set of instructions for controlling a radiation treatment delivery system operatively connected to the computing device, comprising:
- obtaining, by the at least one processor, a plurality of positions for a plurality of mechanical and radiation producing components of the radiation treatment delivery system defined by a radiotherapy treatment plan;
- obtaining, by the at least one processor, a set of position related constraints for the plurality of mechanical and radiation producing components of the radiation treatment delivery system, the constraints applicable to the radiation treatment delivery system delivering the radiotherapy treatment plan by synchronous motion of the plurality of mechanical and radiation producing components traversing a prescribed sequence of the plurality of positions in a predetermined time, as defined by the radiotherapy treatment plan;
- determining, by the at least one processor, a trajectory and a minimum duration for the radiation treatment delivery system to traverse the prescribed sequence of the plurality of positions and deliver the radiotherapy treatment plan as defined by the radiotherapy treatment plan while adhering to the constraints for the plurality of mechanical and radiation producing components of the radiation treatment delivery system and being within a predetermined tolerance limit of a linear trajectory along the prescribed sequence of the plurality of positions;
- generating, by the at least one processor, a record of the determined trajectory and minimum duration for the radiation treatment delivery system to traverse the prescribed sequence of the plurality of positions and deliver the radiotherapy treatment plan; and
- controlling, by the at least one processor, the plurality of mechanical and radiation producing components of the radiation treatment delivery system to execute, in synchronous motion, the determined trajectory within the determined minimum duration, as indicated in the record.

7. The method of claim 6, wherein the constraints include, for each of the plurality of mechanical and radiation producing components of the radiation treatment delivery system, boundary constraints, constraints on derivatives of the position during the trajectory, and trajectory deviation tolerance constraints.

8. The method of claim 7, wherein the boundary constraints include at least an entry velocity, an exit velocity, an entry acceleration, an exit acceleration, a time to execute the trajectory, and a distance between trajectory entry and exit positions.

9. The method of claim 8, wherein the entry acceleration and the exit acceleration are equal to zero.

10. The method of claim 7, wherein the constraints on derivatives of the position during the trajectory include those on one or more of: a jerk, an acceleration, and a velocity.

11. The method of claim 8, wherein the distance between trajectory entry and exit positions is a predefined value.

12. The method of claim 6, wherein the motion of the plurality of mechanical and radiation producing components is defined by a velocity model having three phases, including, in order, a first monotonic velocity phase, a constant velocity phase, and a second monotonic velocity phase, the first monotonic velocity phase and the second monotonic velocity phase being opposite directions of each other.

13. The method of claim 6, further comprising determining a corresponding delivery dose for the determined trajectory and minimum duration.

14. The method of claim 6, further comprising, in response to an interruption in the execution of the determined trajectory within the determined minimum duration:
- determining a resumption trajectory for the radiation treatment delivery system to return to the determined trajectory from an interruption position within a minimum number of the plurality of positions of the radiotherapy treatment plan; and
- returning to the determined trajectory by appending the resumption trajectory to a remaining portion of the determined trajectory after the interruption position.

15. The method of claim 6, determining a trajectory and a minimum duration comprising:
- permitting at least some of the plurality of mechanical and radiation producing components of the radiation treatment delivery system to have a non-zero value for at least one of an entry velocity and an exit velocity for a shoot segment of a step-and-shoot radiotherapy treatment plan;
- permitting the at least some of the plurality of mechanical and radiation producing components of the radiation treatment delivery system to move within a predetermined toleration of the trajectory of the step-and-shoot radiotherapy treatment plan; and
- determining a trajectory for the radiation treatment delivery system to traverse the prescribed sequence of the plurality of positions of the step-and-shoot radiotherapy treatment plan, and the duration of the step-and-shoot radiotherapy treatment plan being reduced.

16. A non-transitory medium storing processor-executable program instructions, the instructions, when executed by a processor, causing the processor to:
- obtain a plurality of positions for a plurality of mechanical and radiation producing components of a radiation treatment delivery system defined by a radiotherapy treatment plan;
- obtain a set of position related constraints for the plurality of mechanical and radiation producing components of the radiation treatment delivery system, the constraints applicable to the radiation treatment delivery system delivering the radiotherapy treatment plan by synchronous motion of the plurality of mechanical and radiation producing components traversing a prescribed sequence of the plurality of positions in a predetermined time, as defined by the radiotherapy treatment plan;
- determine a trajectory and a minimum duration for the radiation treatment delivery system to traverse the prescribed sequence of the plurality of positions and deliver the radiotherapy treatment plan as defined by the radiotherapy treatment plan while adhering to the constraints for the plurality of mechanical and radiation producing components of the radiation treatment delivery system and being within a predetermined tolerance limit of a linear trajectory along the prescribed sequence of the plurality of positions;
- generate a record of the determined trajectory and minimum duration for the radiation treatment delivery system to traverse the prescribed sequence of the plurality of positions and deliver the radiotherapy treatment plan; and
- control the plurality of mechanical and radiation producing components of the radiation treatment delivery system to execute, in synchronous motion, the determined trajectory within the determined minimum duration, as indicated in the record.

17. The medium of claim 16, wherein the constraints include, for each of the plurality of mechanical and radiation producing components of the radiation treatment delivery system, boundary constraints, constraints on derivatives of the position during the trajectory, and trajectory deviation tolerance constraints.

18. The medium of claim 17, wherein the boundary constraints include at least an entry velocity, an exit velocity, an entry acceleration, an exit acceleration, a time to execute the trajectory, and a distance between trajectory entry and exit positions.

19. The medium of claim 18, wherein the entry acceleration and the exit acceleration are equal to zero.

20. The medium of claim 17, wherein the constraints on derivatives of the position during the trajectory include, at a least jerk, an acceleration, and a velocity.

21. The medium of claim 18, wherein the distance between trajectory entry and exit positions is a predefined value.

22. The medium of claim 16, wherein the motion of the plurality of mechanical and radiation producing components is defined by a velocity model having three phases, including, in order, a first monotonic velocity phase, a constant velocity phase, and a second monotonic velocity phase, the first monotonic velocity phase and the second monotonic velocity phase being opposite directions of each other.

23. The medium of claim 16, further causing the processor to determine a corresponding delivery dose for the determined trajectory and minimum duration.

24. The medium of claim 16, further causing the processor to, in response to an interruption in the execution of the determined trajectory within the determined minimum duration:
   determine a resumption trajectory for the radiation treatment delivery system to return to the determined trajectory from an interruption position within a minimum number of the plurality of positions of the radiotherapy treatment plan; and
   return to the determined trajectory by appending the resumption trajectory to a remaining portion of the determined trajectory after the interruption position.

25. The medium of claim 16, further causing the processor to:
   permit at least some of the plurality of mechanical and radiation producing components of the radiation treatment delivery system to have a non-zero value for at least one of an entry velocity and an exit velocity for a shoot segment of a step-and-shoot radiotherapy treatment plan;
   permit the at least some of the plurality of mechanical and radiation producing components of the radiation treatment delivery system to move within a predetermined toleration of the trajectory of the step-and-shoot radiotherapy treatment plan; and
   determine a modified trajectory for the radiation treatment delivery system to traverse the prescribed sequence of the plurality of positions of the step-and-shoot radiotherapy treatment plan, the duration of the step-and-shoot radiotherapy treatment plan being reduced.

26. A method implemented on a computing device having at least one processor and a storage device storing a set of instructions for controlling a imaging system operatively connected to the computing device, comprising:
   obtaining, by the at least one processor, a plurality of positions for a plurality of mechanical and radiation producing components of the imaging system defined by an imaging plan;
   obtaining, by the at least one processor, a set of position related constraints for the plurality of mechanical and radiation producing components of the imaging system, the constraints applicable to the imaging plan by synchronous motion of the plurality of mechanical and radiation producing components traversing a prescribed sequence of the plurality of positions in a predetermined time, as defined by the imaging plan;
   determining, by the at least one processor, a trajectory and a minimum duration for the radiation treatment delivery system to traverse the prescribed sequence of the plurality of positions and deliver the imaging plan while adhering to the constraints for the plurality of mechanical and radiation producing components of the imaging system and being within a predetermined tolerance limit of a linear trajectory along the prescribed sequence of the plurality of positions;
   generating, by the at least one processor, a record of the determined trajectory and minimum duration for the imaging system to traverse the prescribed sequence of the plurality of positions and deliver the imaging plan; and
   controlling, by the at least one processor, the plurality of mechanical and radiation producing components of the imaging system to execute, in synchronous motion, the determined trajectory within the determined minimum duration, as indicated in the record.

27. The method of claim 26, wherein the constraints include, for each of the plurality of mechanical and radiation producing components of the imaging system, boundary constraints, constraints on derivatives of the position during the trajectory, and trajectory deviation tolerance constraints.

28. The method of claim 27, wherein the boundary constraints include at least an entry velocity, an exit velocity, an entry acceleration, an exit acceleration, a time to execute the trajectory, and a distance between trajectory entry and exit positions.

29. The method of claim 28, wherein the entry acceleration and the exit acceleration are equal to zero.

30. The method of claim 27, wherein the constraints on derivatives of the position during the trajectory include those on one or more of: a jerk, an acceleration, and a velocity.

31. The method of claim 28, wherein the distance between trajectory entry and exit positions is a predefined value.

32. The method of claim 26, wherein the motion of the plurality of mechanical and radiation producing components is defined by a velocity model having three phases, including, in order, a first monotonic velocity phase, a constant velocity phase, and a second monotonic velocity phase, the first monotonic velocity phase and the second monotonic velocity phase being opposite directions of each other.

33. The method of claim 26, further comprising determining a corresponding delivery dose for the determined trajectory and minimum duration.

34. The method of claim 26, further comprising, in response to an interruption in the execution of the determined trajectory within the determined minimum duration:
   determining a resumption trajectory for the imaging system to return to the determined trajectory from an interruption position within a minimum number of the plurality of positions of the imaging plan; and returning to the determined trajectory by appending the resumption trajectory to a remaining portion of the determined trajectory after the interruption position.

35. The method of claim 26, determining a trajectory and a minimum duration comprising:
- permitting at least some of the plurality of mechanical and radiation producing components of the imaging system to have a non-zero value for at least one of an entry velocity and an exit velocity for a part of the imaging plan that calls for a stationary interval;
- permitting the at least some of the plurality of mechanical and radiation producing components of the imaging system to move within a predetermined toleration of the trajectory of the imaging plan that calls for a stationary interval; and
- determining a trajectory for the imaging system to traverse the prescribed sequence of the plurality of positions of the imaging plan that calls for a stationary interval, and the duration of the imaging plan being reduced.

* * * * *